(12) United States Patent
Jolidon et al.

(10) Patent No.: US 7,553,862 B2
(45) Date of Patent: Jun. 30, 2009

(54) 4-AMINO-1,5-SUBSTITUTED-1,5-DIHYDRO-IMIDAZOL-2-ONES

(75) Inventors: Synese Jolidon, Blauen (CH); Robert Narquizian, Saint Louis (FR); Roger Norcross, Olsberg (CH); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 158 days.

(21) Appl. No.: 11/712,783

(22) Filed: Mar. 1, 2007

(65) Prior Publication Data

US 2007/0213384 A1 Sep. 13, 2007

(30) Foreign Application Priority Data

Mar. 8, 2006 (EP) .................................. 06110812

(51) Int. Cl.
A61K 31/4166 (2006.01)
C07D 233/32 (2006.01)

(52) U.S. Cl. .................. 514/397; 514/398; 514/401; 548/311.1; 548/326.5

(58) Field of Classification Search ............. 548/311.1, 548/326.5; 514/397, 398, 401
See application file for complete search history.

(56) References Cited

FOREIGN PATENT DOCUMENTS

WO   WO 2005/040166   5/2005

OTHER PUBLICATIONS

CAPLUS Accession No. 1964:469124, abstract of Bala et al, "5,6-Dimethylbenzimidazole, synthetic precursor in the microbiological production of vitamin B12," Pharmazie (1964).*
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell, vol. 98, pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Liebigs, Ann. Chem. 80: pp. 80-82 (1963) (English language translation attached).
Chem. Ber. vol. 97: 2276 (1964).
Chemical Abstract XP002435251.
Chemical Abstract XP002435252.
Chemical Abstract XP002436293.

* cited by examiner

*Primary Examiner*—Rei-Tsang Shiao
*Assistant Examiner*—Janet L Coppins
(74) *Attorney, Agent, or Firm*—George W. Johnston; Patricia S. Rocha-Tramaloni; Kimberly J. Prior

(57) ABSTRACT

The present invention relates to compounds of formula I wherein
$R^1$, $R^2$,
$R^3$, and
$R^4$ are as defined herein
and to pharmaceutically acceptable acid addition salts thereof. Compounds of formula I or their tautomeric forms are good inhibitors of the glycine transporter 1 (GlyT-1), and have a good selectivity to glycine transporter 2 (GlyT-2) inhibitors. Such compounds are useful for the treatment of schizophrenia.

19 Claims, No Drawings

4-AMINO-1,5-SUBSTITUTED-1,5-DIHYDRO-IMIDAZOL-2-ONES

PRIORITY TO RELATED APPLICATIONS

This application claims the benefit of European Application No. 06110812.2, filed Mar. 8, 2006, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly address negative and cognitive symptoms which are the redictors of functional outcome (Sharma T., *Br. J. Psychiatry*, 174(suppl. 28): 44-51, 1999).

A complementary model of schizophrenia was proposed in the mid-1960s based upon the psychotomimetic action caused by the blockade of the glutamate system by compounds like phencyclidine (PCP) and related agents (ketamine) which are non-competitive NMDA receptor antagonists. Interestingly, in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999). Furthermore transgenic mice expressing reduced levels of the NMDAR1 subunit display behavioral abnormalities similar to those observed in pharmacologically induced models of schizophrenia, supporting a model in which reduced NMDA receptor activity results in schizophrenia-like behavior (Mohn A R et al., *Cell*, 98: 427-236, 1999).

Glutamate neurotransmission, in particular NMDA receptor activity, plays a critical role in synaptic plasticity, learning and memory, such that NMDA receptors appear to serve as a graded switch for gating the threshold of synaptic plasticity and memory formation (Wiley, N.Y.; Bliss TV and Collingridge G L, *Nature*, 361: 31-39, 1993). Transgenic mice overexpressing the NMDA NR2B subunit exhibit enhanced synaptic plasticity and superior ability in learning and memory (Tang J P et al., *Natur*, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters act by removing neurotransmitters from the extracellular space, and can control their extracellular lifetime and thereby modulate the magnitude of the synaptic transmission (Gainetdinov R R et al, *Trends in Pharm. Sci.*, 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA*, 95: 15730-15734, 1998; Chen L. et al., *J. Neurophysiol.*, 89(2): 691-703, 2003).

Glycine transporter inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans,.* 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of \formula I

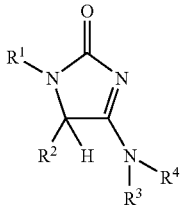

wherein
R¹ is —(CH$_2$)$_n$-aryl or —(CH$_2$)$_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
R² is —(CH$_2$)$_n$-aryl or —(CH$_2$)$_n$-heteroaryl, wherein such groups are unsubstituted or substituted by one or more substituents selected from the group consisting of lower alkyl, lower alkoxy, halogen and —N(lower alkyl)$_2$;
R³ is hydrogen or lower alkyl;
R⁴ is —(CH$_2$)$_n$-aryl or —(CH$_2$)$_n$-heteroaryl, wherein such groups are unsubstituted and substituted by one or more substituents selected from the group consisting of halogen or lower alkoxy, or is lower alkyl, or —(CH$_2$)$_n$-cycloalkyl; or
R³ and R⁴ form together with the N-atom to which they are attached a heterocyclic ring; and
n is 0, 1 or 2;

and pharmaceutically acceptable acid addition salts thereof.
If R³ is hydrogen, the structure of formula I includes also its tautomeric form of formula IA

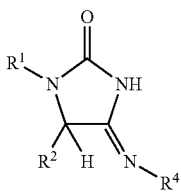

wherein
R¹ is —(CH$_2$)$_n$-aryl or —(CH$_2$)$_n$-heteroaryl, wherein such groups are unsubstituted or substituted by one or more substituents, selected from the group consisting of halogen, lower alkyl substituted by halogen, lower alkoxy, lower alkyl, cyano, nitro, —O-lower alkyl substituted by halogen or morpholinyl;
R² is —(CH$_2$)$_n$-aryl or —(CH$_2$)$_n$-heteroaryl, wherein such groups are unsubstituted or substituted by one or more substituents, selected from the group consisting of lower alkyl, lower alkoxy, halogen or —N(lower alkyl)$_2$;
R⁴ is —(CH$_2$)$_n$-aryl or —(CH$_2$)$_n$-heteroaryl, wherein such groups are unsubstituted or substituted by one or more substituents, selected from the group consisting of halogen or lower alkoxy, or is lower alkyl, —(CH$_2$)$_n$-cycloalkyl; and n is 0, 1 or 2;

and to pharmaceutically acceptable acid addition salts thereof.

The invention also provides all pharmaceutically active salts of compounds of formula I, all racemic mixtures, all their corresponding enantiomers and/or optical isomers and tautomeric forms.

The invention also provides pharmaceutical compositions containing one or more compound of the invention, for example a compound of formula I or IA, and a pharmaceutically acceptable carrier. The present invention further provides methods for the manufacture of the compounds and compositions of the invention.

Compounds of formula I or IA are good inhibitors of the glycine transporter 1 (GlyT-1) and have a good selectivity to glycine transporter 2 (GlyT-2) inhibitors. Thus, the invention also provides methods for the treatment of diseases related to activation of NMDA receptors via Glyt-1 inhibition, for example neurological and neuropsychiatric disorders. In particular the invention provides methods for the treatment of psychoses, dysfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 6 carbon atoms, for example, methyl, ethyl, propyl, isopropyl, n-butyl, i-butyl, 2-butyl, t-butyl and the like. Preferred alkyl groups are those with 1-4 carbon atoms.

As used herein, the term "cycloalkyl" denotes a saturated alicyclic ring containing from 3 to 6 carbon atoms.

As used herein, the term "lower alkoxy" denotes a saturated straight- or branched-chain hydrocarbon group containing from 1 to 6 carbon atoms as described above, which is connected via an oxygen atom.

The term "halogen" denotes chlorine, iodine, fluorine and bromine.

The term "aryl" denotes a monovalent cyclic aromatic hydrocarbon radical containing from 6 to 10 ring atoms and consisting of one ring or two fused rings in which at least one ring is aromatic in nature, for example phenyl, benzyl, naphthyl or biphenyl.

The term "heteroaryl" denotes a monovalent aromatic carbocyclic radical containing from 6 to 10 ring atoms consisting of one ring or two fused rings, which contains at least one heteroatom, for example pyridyl, pyrazolyl, furanyl or thiophenyl.

The term "alkyl substituted by halogen" denotes an alkyl group as defined above in which one or more hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ and $CH(CH_2F)CH_2F$.

The term "heterocyclic ring" denotes a saturated or partially saturated ring system, wherein an N-atom is in 1-position, for example azepan-1-yl or 3,4-dihydro-isoquinolin-1-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of \formula I

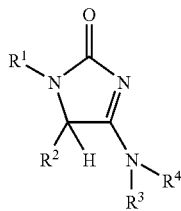

I wherein
$R^1$ is —$(CH_2)_n$-aryl or —$(CH_2)_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
$R^2$ is —$(CH_2)_n$-aryl or —$(CH_2)_n$-heteroaryl, wherein such groups are unsubstituted or substituted by one or more substituents selected from the group consisting of lower alkyl, lower alkoxy, halogen and —N(lower alkyl)$_2$;
$R^3$ is hydrogen or lower alkyl;
$R^4$ is —$(CH_2)_n$-aryl or —$(CH_2)_n$-heteroaryl, wherein such groups are unsubstituted and substituted by one or more substituents selected from the group consisting of halogen or lower alkoxy, or is lower alkyl, or —$(CH_2)_n$-cycloalkyl; or
$R^3$ and $R^4$ form together with the N-atom to which they are attached a heterocyclic ring; and
n is 0, 1 or 2;

and pharmaceutically acceptable acid addition salts thereof.

If $R^3$ is hydrogen, the structure of formula I includes also its tautomeric form of formula IA

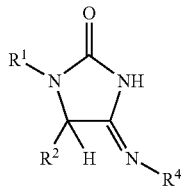

IA wherein
$R^1$ is —$(CH_2)_n$-aryl or —$(CH_2)_n$-heteroaryl, wherein such groups are unsubstituted or substituted by one or more substituents, selected from the group consisting of halogen, lower alkyl substituted by halogen, lower alkoxy, lower alkyl, cyano, nitro, —O-lower alkyl substituted by halogen or morpholinyl;
$R^2$ is —$(CH_2)_n$-aryl or —$(CH_2)_n$-heteroaryl, wherein such groups are unsubstituted or substituted by one or more substituents, selected from the group consisting of lower alkyl, lower alkoxy, halogen or —N(lower alkyl)$_2$;
$R^4$ is —$(CH_2)_n$-aryl or —$(CH_2)_n$-heteroaryl, wherein such groups are unsubstituted or substituted by one or more substituents, selected from the group consisting of halogen or lower alkoxy, or is lower alkyl, —$(CH_2)_n$-cycloalkyl;
and
n is 0, 1 or 2;

and to pharmaceutically acceptable acid addition salts thereof.

The invention also provides all pharmaceutically active salts of compounds of formula I, all racemic mixtures, all their corresponding enantiomers and/or optical isomers and tautomeric forms.

Preferred compounds of the present invention are compounds of formula I, wherein $R^1$ is phenyl substituted by halogen, $R^2$ is phenyl and $R^4$ is benzyl, for example
(Rac)-4-benzylamino-1-(4-chloro-phenyl)-5-phenyl-1,5-dihydro-imidazol-2-one
(Rac)-4-benzylamino-1-(3,4-dichloro-phenyl)-5-phenyl-1,5-dihydro-imidazol-2-one and
(−)-4-benzylamino-1-(4-chloro-phenyl)-5-phenyl-1,5-dihydro-imidazol-2-one.

Preferred compounds of the present invention are further compounds of formula I, wherein $R^1$ is phenyl substituted by halogen, $R^2$ is phenyl substituted by lower alkyl and $R^4$ is benzyl, for example
(Rac)-4-benzylamino-1-(3,4-dichloro-phenyl)-5-p-tolyl-1,5-dihydro-imidazol-2-one and
(Rac)-4-benzylamino-1-(3,4-dichloro-phenyl)-5-(3,4-dimethyl-phenyl)-1,5-dihydro-imidazol-2-one.

Preferred compounds of the present invention are compounds of formula I, wherein $R^1$ and $R^2$ are phenyl substituted by halogen and $R^4$ is benzyl, for example
(Rac)-4-benzylamino-5-(4-chloro-phenyl)-1-(3,4-dichloro-phenyl)-1,5-dihydro-imidazol-2-one
(Rac)-4-benzylamino-1-(3,4-dichloro-phenyl)-5-(4-fluoro-phenyl)-1,5-dihydro-imidazol-2-one and
(Rac)-4-benzylamino-1-(3-chloro-4-fluoro-phenyl)-5-(4-fluoro-phenyl)-1,5-dihydro-imidazol-2-one.

Preferred compounds of the present invention are compounds of formula I, wherein $R^1$ is phenyl substituted by halogen, $R^2$ is phenyl substituted by methoxy and $R^4$ is benzyl, for example
(Rac)-4-benzylamino-1-(3,4-dichloro-phenyl)-5-(3-methoxy-phenyl)-1,5-dihydro-imidazol-2-one.

Preferred compounds of the present invention are further compounds of formula I, wherein $R^1$ is phenyl substituted by halogen, $R^2$ is phenyl and $R^4$ is benzyl substituted by halogen, for example
Rac-1-(3,4-dichloro-phenyl)-4-(4-fluorobenzylamino)-5-phenyl-1,5-dihydro-imidazol-2-one.

Preferred compounds of the present invention are further compounds of formula I, wherein $R^1$ is phenyl substituted by halogen, $R^2$ is phenyl and $R^4$ is lower alkyl, for example
Rac-1-(3,4-dichloro-phenyl)-4-(3-methyl-butylamino)-5-phenyl-1,5-dihydroimidazol-2-one and (Rac)-1-(3,4-dichloro-phenyl)-4-hexylamino-5-phenyl-1,5-dihydro-imidazol-2-one.

Preferred compounds of the present invention are further compounds of formula I, wherein $R^1$ is phenyl substituted by halogen, $R^2$ is phenyl and $R^4$ is —$CH_2$-cycloalkyl, for example (Rac)-4-(cyclohexylmethyl-amino)-1-(3,4-dichloro-phenyl)-5-phenyl-1,5-dihydro-imidazol-2-one.

The present compounds of formula I and their pharmaceutically acceptable salts can be prepared by methods known in the art, for example, by processes (a) or (b) described below, which process comprises a) brominating a compound of formula

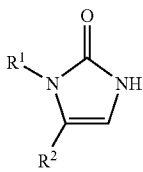

II followed by reaction with an amine of formula $NHR^3R^4$ to obtain a compound of formula

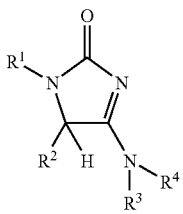

I wherein the substituents $R^1$, $R^2$, $R^3$ and $R^4$ are as defined above, or b) reacting in one step a primary amine of formula $R^2NH_2$ (III), together with potassium cyanate, an isonitrile of formula

(V)

and an aldehyde of formula $R^1C(O)H$ (IV) to obtain a compound of formula

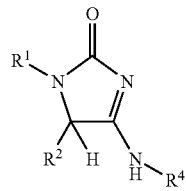

I-1 wherein the substituents $R^1$, $R^2$ and $R^4$ are as defined above, and if desired, converting the compounds obtained into pharmaceutically acceptable acid addition salts.

The compounds of formula I can be prepared in accordance with process variants (a) or (b) and with the following schemes 1 or 2. The starting materials are either commercially available, are otherwise known in the chemical literature, or can be prepared in accordance with methods well known in the art.

Scheme 1

A 4-step-synthesis is shown in scheme 1

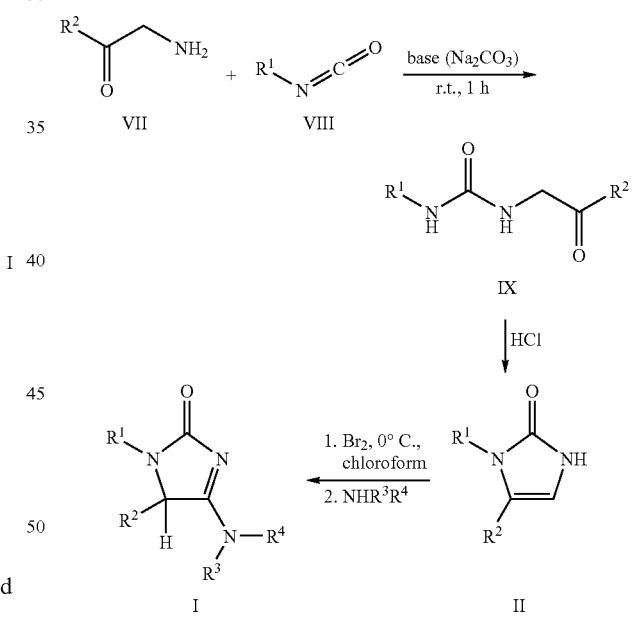

1) Reaction of an isocyanate with an amino ketone in the presence of a base to yield the 3-(2-oxo)-urea derivatives.
2) Cyclization of 3-(2-oxo)-urea derivatives in the presence of concentrated hydrochloric acid leads to the formation of 1,5-substituted-1,3,dihydro-imidizol-2-one derivatives.
3) Bromination of 1,5-substituted-1,3-dihydro-imidizol-2-one derivatives,
4) followed by reaction with primary amines leads to formation of compounds of general structure I.

Step 1: Synthesis of Ureas of Formula IX

To a suspension of a compound of formula VIII and of a compound of formula VII is added an aqueous solution of sodium carbonate. The reaction mixture is stirred overnight at room temperature affording a precipitate which is filtered off. The precipitate is worked up in conventional manner.

Step 2: Synthesis of 1,3-dihydro-imidazol-2-ones of Formula II

Concentrated hydrochloric acid is added to a compound of formula IX to form a suspension at room temperature. The reaction mixture is stirred for one week until the suspension had transformed into a corresponding compound of formula II.

Steps 3 and 4: Bromination and Amination of 1,5-diphenyl-1,3-dihydro-imidazol-2-ones To a solution of a compound of formula II in dry chloroform in the presence of molecular sieves (4 Å), a solution of bromine in chloroform is added dropwise using a syringe. The reaction mixture is stirred at 0° C. until completion of bromination is observed by TLC. An amine of formula $NHR^3R^4$ is then added via a syringe and the reaction is allowed to warm to room temperature and is then heated to about 65° C. for 24 hours. The reaction is carried under nitrogen throughout.

Compounds of formula I can further be prepared by Ugi's reaction (*Liebigs Ann. Chem.*, 1963, 80, 670 or *Chem. Ber.*, 1964, 97, 2276, or *Angew. Chem.*, 1962, 74, 9). This is a one step reaction of primary amines, potassium cyanate, isonitriles and aldehydes or ketones, as shown in scheme 2.

Scheme 2

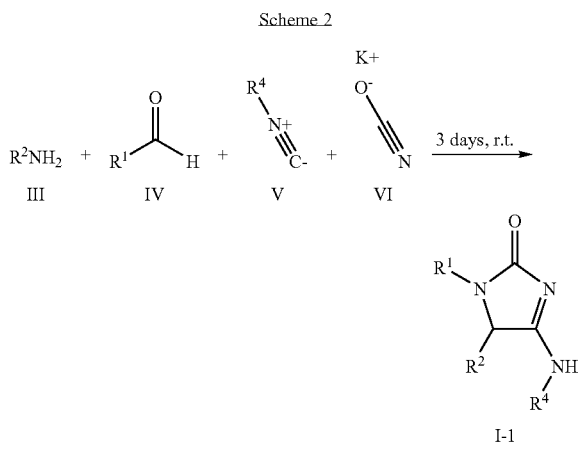

A mixture of an aldehyde of formula IV and a corresponding isocyanide of formula V in methanol is treated with a solution of potassium cyanate of formula VI in water. A compound of formula III and pyridinium hydrochloride is added and the mixture is stirred at room temperature for about 48 hours. The solid form is filtered off and triturated with diethyl ether to give the compound of formula I-1 or the corresponding tautomere.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I can be basic, for example in cases where the residue $R^3$ contains a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin1% (Gibco life technologies), Hygromycin 0.6 mg/ml (Gibco life technologies), Glutamine 1 mM Gibco life technologies) Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (µM) at GlyT-1 in the range of 0.007-0.1. Values for representative compounds are shown in the table below.

| Example | IC$_{50}$ (µM) |
|---------|----------------|
| 10 | 0.062 |
| 13 | 0.076 |
| 24 | 0.04 |
| 25 | 0.057 |
| 28 | 0.035 |
| 41 | 0.072 |
| 43 | 0.03 |
| 44 | 0.058 |
| 50 | 0.062 |
| 51 | 0.007 |
| 53 | 0.082 |
| 57 | 0.077 |
| 58 | 0.024 |

The present invention also provides pharmaceutical compositions containing compounds of the invention, for example compounds of formula I or IA, and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. In particular, the present invention provides a method for treating schizophrenia, which comprises administering a therapeutically effective amount of a compound of formula I or a pharmaceutically acceptable salt thereof. The invention also provides a method of treating cognitive impairment, which comprises administering a therapeutically effective amount of a compound of formula I or a pharmaceutically acceptable salt thereof. The invention further provides a method for the treatment of Alzheimer's disease, which comprises administering a therapeutically effective amount of a compound of formula I or a pharmaceutically acceptable salt thereof. The most preferred indications in accordance with the present invention are schizophrenia, cognitive impairment and Alzheimer's disease.

The compounds and compositions of the invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention can be administered rectally, for example, in the form of suppositories or parenterally, for example, in the form of injectable solutions.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or IA or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I or IA | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I or IA | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope but merely as being representative thereof. Unless otherwise indicated, the following examples have been performed, regardless of the tense in which they are written.

EXAMPLE 1

4-Benzylamino-1-(2,4-difluoro-phenyl)-5-phenyl-1,5-dihydro-imidazol-2-one

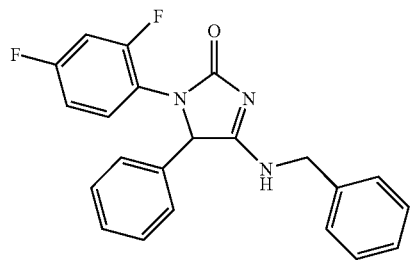

A mixture of 2.32 mmol benzaldehyde and 2.32 mmol benzylisocyanide in 1 ml methanol was treated with a solution of 2.32 mmol potassium cyanate in 0.5 ml water. 2.32 mmol of 2,4-difluoroaniline and 2.32 mmol of pyridinium hydrochloride was added and the mixture stirred at room temperature for 48 hours. The solid formed was filtered off and triturated with diethyl ether to give 103 mg of the title compound as a slightly brown solid. Yield=12%. MS (m/e): 378.5 (100%; M+H$^+$), 400.1 (46%; M+Na).

EXAMPLE 2 rac-4-Benzylamino-1,5-diphenyl-1,5-dihydro-imidazol-2-one

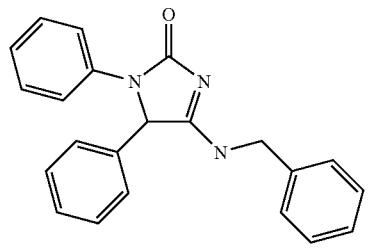

The title compound can be prepared in a similar way as example 1 from benzaldehyde, benzylisocyanide, and aniline. MS (m/e): 340.3 (M–H).

EXAMPLE 3 rac-4-Benzylamino-5-phenyl-1-p-tolyl-1,5-dihydro-imidazol-2-one

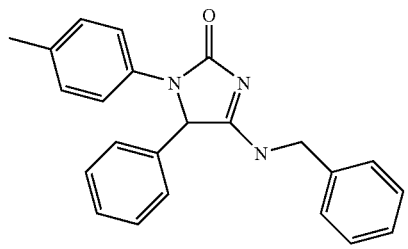

The title compound can be prepared in a similar way as example 1 from benzaldehyde, benzylisocyanide, and 4-methylaniline. MS (m/e): 354.3 (M–H).

EXAMPLE 4 rac-4-Benzylamino-5-phenethyl-1-phenyl-1,5-dihydro-imidazol-2-one

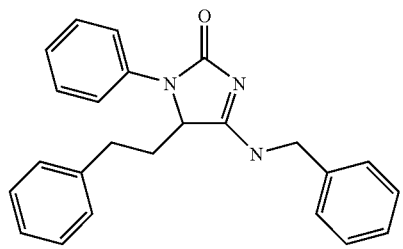

The title compound can be prepared in a similar way as example 1 from 3-phenylproprioaldehyde, benzylisocyanide, and aniline. MS (m/e): 368.3 (M–H).

EXAMPLE 5 rac-4-Benzylamino-1-(3,4-dichloro-phenyl)-5-phenethyl-1,5-dihydro-imidazol-2-one

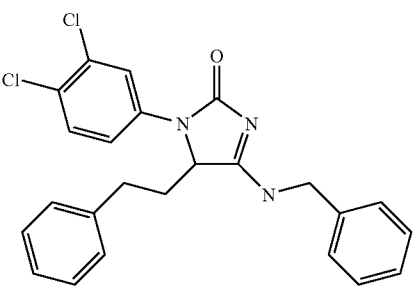

The title compound can be prepared in a similar way as example 1 from 3-phenylproprioaldehyde, benzylisocyanide, and 3,4-dichloroaniline. MS (m/e): 436.1 (M–H).

EXAMPLE 6 rac-1-Benzyl-4-benzylamino-5-phenethyl-1,5-dihydro-imidazol-2-one

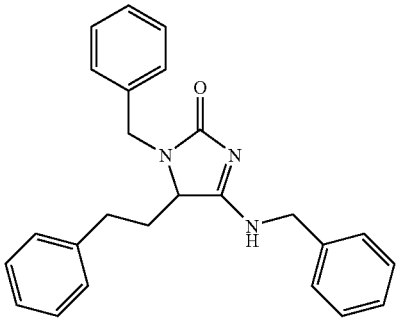

The title compound can be prepared in a similar way as example 1 from 3-phenylproprioaldehyde, benzylisocyanide, and benzylamine. MS (m/e):384 (M+H+).

EXAMPLE 7

4-Benzylamino-5-phenyl-1-(4-trifluoromethyl-phenyl)-1,5-dihydro-imidazol-2-one

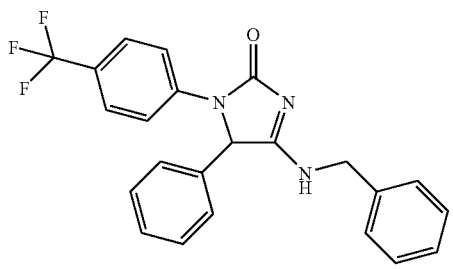

Prepared in analogy to example 1 from benzaldehyde, benzylisocyanide, potassium cyanate, 4-aminobenzotrifluoride and pyridinium hydrochlorideas a light brown solid. Yield=51%. MS (m/e): 410.3 (100%; M+H$^+$), 432.3 (21%; M+Na).

EXAMPLE 8

(Rac)-4-benzylamino-1-(4-methoxy-phenyl)-5-phenyl-1,5-dihydro-imidazol-2-one

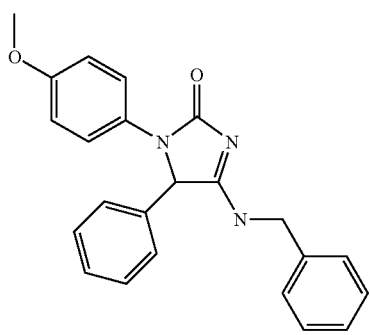

Similarly to compound 1, p-anisidine, benzaldehyde and benzylisocyanide afforded the title compound as a black solid (130 mg, 41%). $\delta_H$ NMR (CDCl$_3$, 300 MHz) 7.38-7.18 (10H, m, H arom), 6.76 (4H, d, J=9.1 Hz, H arom), 5.51 (1H, s, C$_5$H), 5.20 (1H, br signal, NH), 4.72 (1H, dd, J=14.9, 6.1 Hz, CH$_A$H$_B$Ph), 4.54 (1H, dd, J=14.7, 5.3 Hz, CH$_A$H$_B$Ph), 3.71 (3H, s, OCH$_3$); m/z (EI) 372.1 (100%, M+H$^+$).

EXAMPLE 9

(Rac)-4-benzylamino-1-(4-methoxy-phenyl)-5-phenyl-1,5-dihydro-imidazol-2-one hydrochloride

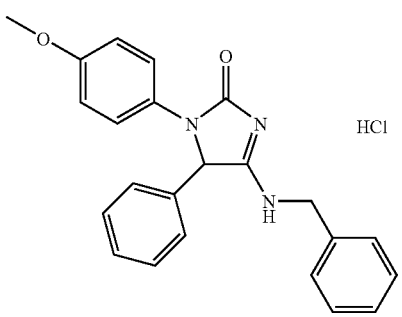

20 mg of (Rac)-4-benzylamino-1-(4-methoxy-phenyl)-5-phenyl-1,5-dihydro-imidazol-2-one was stirred for 2 hours at room temperature in a solution of 3N HCl in methanol. Evaporation of the solvent gave the title compound. m/z (EI) 372.2 (100%, M+H$^+$).

EXAMPLE 10

(Rac)-4-benzylamino-1-(4-chloro-phenyl)-5-phenyl-1,5-dihydro-imidazol-2-one

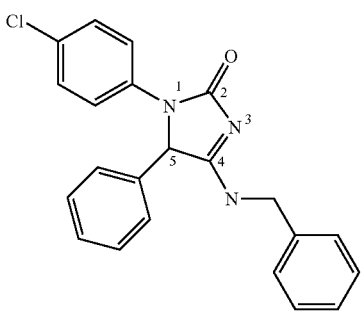

The numbers in the formula are aimed for characterizing NMR-spectra. To a solution of benzaldehyde (1 equiv., 0.85 mmol, 94 µL) and benzylisocyanide (1 equiv., 0.85 mmol, 92 µL) in methanol (0.6 mL) was added KOCN (1 equiv., 0.85 mmol, 68 mg) in H$_2$O (0.3 mL) followed by 4-chloroaniline (1 equiv., 0.85 mmol, 98 mg) and pyridinium hydrochloride (1 equiv., 0.85 mmol). The reaction was stirred at room temperature for 3 days and the precipitate filtered. Work-up and purification afforded (rac)-4-benzylamino-1-(4-chloro-phenyl)-5-phenyl-1,5-dihydro-imidazol-2-one (117 mg, 37%) as an amber solid. $\delta_H$ NMR (CDCl$_3$, 300 MHz) 7.45-7.10 (14H, m, H arom), 5.54 (1H, s, C$_5$H), 5.35 (1H, br signal, NH), 4.71

(1H, dd, J=14.5, 5.6 Hz, CH$_A$H$_B$Ph), 4.52 (1H, dd, J=14.5, 4.1 Hz, CH$_A$H$_B$Ph); m/z (EI) 378.3 (37%), 377.3 (26), 376.3 (100, M+H$^+$).

EXAMPLE 11

(Rac)-4-benzylamino-1-(3,4-dimethyl-phenyl)-5-phenyl-1,5-dihydro-imidazol-2-one

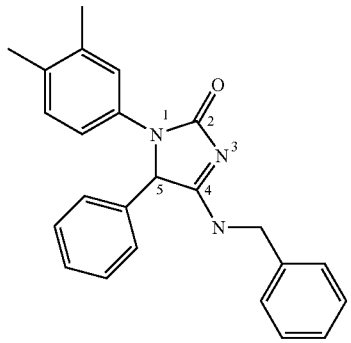

Similarly to compound 1, 3,4-dimethylaniline, benzaldehyde and benzylisocyanide afforded the title compound as a dark green solid (77 mg, 25%). δ$_H$ NMR (CDCl$_3$, 300 MHz) 7.41-7.26 (9H, m, H arom), 7.17 (2H, dd, J=7.4, 3.4 Hz, H arom), 7.02 (1H, dd, J=8.2, 2.3 Hz, H arom), 6.94 (1H, d, J=8.2 Hz, H arom), 5.54 (1H, s, C$_5$H), 5.23 (1H, app t, J=6.5 Hz, NH), 4.71 (1H, dd, J=14.6, 5.9 Hz, CH$_A$H$_B$Ph), 4.53 (1H, dd, J=14.6, 5.5 Hz, CH$_A$H$_B$Ph), 2.16 (3H, s, CH$_3$), 2.12 (3H, s, CH$_3$); m/z (EI) 371.2 (31%), 370.2 (100, M+H$^+$).

EXAMPLE 12

(Rac)-4-benzylamino-1-(4-isopropyl-phenyl)-5-phenyl-1,5-dihydro-imidazol-2-one

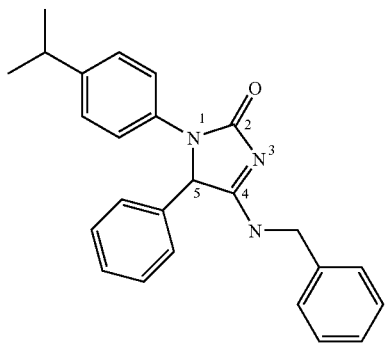

Similarly to compound 1,4-isopropylaniline, benzaldehyde and benzylisocyanide afforded the title compound as a light brown solid (50 mg, 15%). δ$_H$ NMR (CDCl$_3$, 300 MHz) 7.39-7.26 (10H, m, H arom), 7.17-7.14 (2H, m, H arom), 7.07-7.05 (2H, app d, J=9.3 Hz, H arom), 5.56 (1H, s, C$_5$H), 5.37 (1H, app t, J=6.2 Hz, NH), 4.68 (1H, dd, J=14.8, 6.1 Hz, CH$_A$H$_B$Ph), 4.51 (1H, dd, J=14.6, 5.5 Hz, CH$_A$H$_B$Ph), 2.78 (1H, sept, J=7.1 Hz, CH(CH$_3$)$_2$), 1.15 (6H, d, J=7.0 Hz, 2×CH$_3$); m/z (EI) 384.2 (100%, M+H$^+$).

EXAMPLE 13

Rac-4-benzylamino-1-(3,4-dichloro-phenyl)-5-phenyl-1,5-dihydro-imidazol-2-one

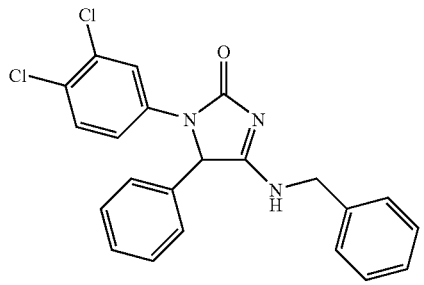

Similarly to compound 1, benzaldehyde, benzylisonitrile, and 3,4,-dichloroaniline, afforded the title compound.

δH NMR (DMSO, 300 MHz) 8.85 (1H, app t, J=6.0 Hz, NH), 7.92 (1H, d, J=2.5 Hz, H arom), 7.46-7.25 (11H, m, H arom), 7.15 (1H, dd, J=7.9, 1.9 Hz, H arom), 6.17 (1H, s, CH), 4.46 (2H, d, J=6.0 Hz, CH$_2$Ph); m/z (EI) 413.2 (14%), 412.2 (43), 411.1 ... 410.1 (M+H+), M−H 408.1, M+H 410.3

EXAMPLE 14

(Rac)-4-benzylamino-1-(4-chloro-3-trifluoromethyl-phenyl)-5-phenyl-1,5-dihydro-imidazol-2-one

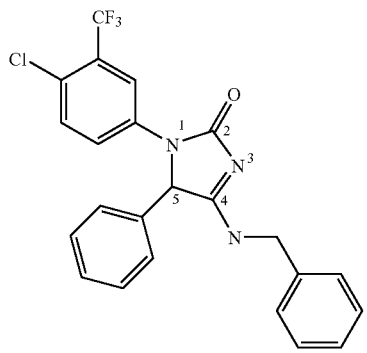

Similarly to compound 1,5-amino-2-chlorobenzyl-trifluoride, benzaldehyde and benzylisocyanide afforded the title compound as a dark brown solid (26 mg, 7%). δ$_H$ NMR (CDCl$_3$, 300 MHz) 7.77 (1H, d, J=2.7 Hz, H arom), 7.66 (1H, dd, J=8.8, 2.6 Hz, H arom), 7.43-7.35 (3H, m, H arom), 7.34-7.23 (6H, m, H arom), 7.14-7.10 (2H, m, H arom), 5.92 (1H, br signal, NH), 5.60 (1H, s, C$_5$H), 4.65 (1H, dd, J=14.9, 5.5 Hz, CH$_A$H$_B$Ph), 4.45 (1H, dd, J=14.7, 4.7 Hz, CH$_A$H$_B$Ph); m/z (EI) 446.2 (26%), 445.2 (28), 444.3 (100, M+H$^+$).

EXAMPLE 15

(Rac)-4-benzylamino-1-(4-isopropyl-phenyl)-5-phenyl-1,5-dihydro-imidazol-2-one

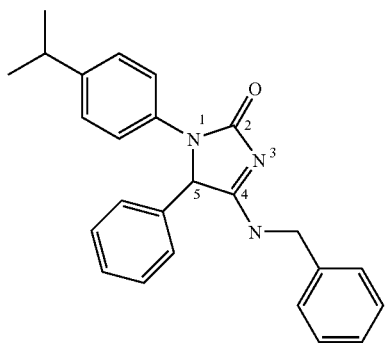

Similarly to compound 1,4-isopropylaniline, benzaldehyde and benzylisocyanide afforded the title compound as a light brown solid (50 mg, 15%). $\delta_H$ NMR (CDCl$_3$, 300 MHz) 7.39-7.26 (10H, m, H arom), 7.17-7.14 (2H, m, H arom), 7.07-7.05 (2H, app d, J=9.3 Hz, H arom), 5.56 (1H, s, C$_5$H), 5.37 (1H, app t, J=6.2 Hz, NH), 4.68 (1H, dd, J=14.8, 6.1 Hz, CH$_A$H$_B$Ph), 4.51 (1H, dd, J=14.6, 5.5 Hz, CH$_A$H$_B$Ph), 2.78 (1H, sept, J=7.1 Hz, CH(CH$_3$)$_2$), 1.15 (6H, d, J=7.0 Hz, 2×CH$_3$); m/z (EI) 384.2 (100%, M+H$^+$).

EXAMPLE 16

(Rac)-4-benzylamino-1-(4-ethyl-phenyl)-5-phenyl-1,5-dihydro-imidazol-2-one

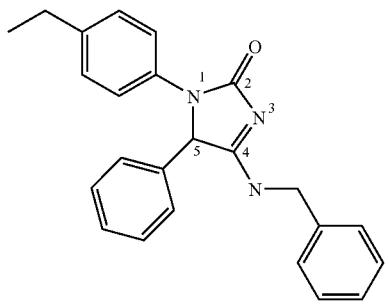

Similarly to compound 1,4-ethylaniline, benzaldehyde and benzylisocyanide afforded the title compound as a light brown solid (60 mg, 19%). $\delta_H$ NMR (CDCl$_3$, 300 MHz) 7.26-7.23 (10H, m, H arom), 7.15-7.12 (2H, m, H arom), 7.02 (2H, d, J=8.5 Hz, H arom), 5.66 (1H, app t, J=5.5 Hz, NH), 5.57 (1H, s, C$_5$H), 4.64 (1H, dd, J=14.9, 6.4 Hz, CH$_A$H$_B$Ph), 4.46 (1H, dd, J=14.8, 5.5 Hz, CH$_A$H$_B$Ph), 2.51 (2H, q, J=7.6 Hz, CH$_3$CH$_2$), 1.13 (3H, t, J=7.6 Hz, CH$_3$CH$_2$); m/z (EI) 370.2 (100%, M+H$^+$).

EXAMPLE 17

(Rac)-4-benzylamino-1-(3,5-dichloro-phenyl)-5-phenyl-1,5-dihydro-imidazol-2-one

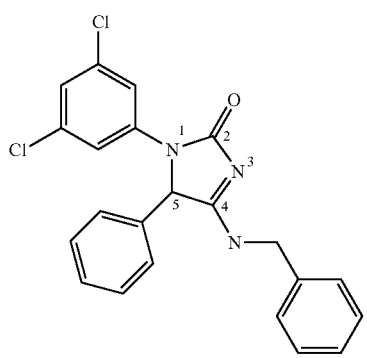

Similarly to compound 1,3,5-dichloroaniline, benzaldehyde and benzylisocyanide afforded the title compound as a dark brown oil (16 mg, 5%). $\delta_H$ NMR (CDCl$_3$, 300 MHz) 7.45-7.37 (5H, m, H arom), 7.35-7.25 (5H, m, H arom), 7.14-7.11 (2H, m, H arom), 6.96 (1H, t, J=1.7 Hz, H arom), 5.65 (1H, br signal, NH), 5.53 (1H, s, C$_5$H), 4.68 (1H, dd, J=14.9, 5.9 Hz, CH$_A$H$_B$Ph), 4.49 (1H, dd, J=14.9, 5.6 Hz, CH$_A$H$_B$Ph); m/z (EI) 412.2 (39%), 410.1 (100, M+H$^+$).

EXAMPLE 18

(Rac)-4-(4-benzylamino-2-oxo-5-phenyl-2,5-dihydro-imidazol-1-yl)-benzonitrile

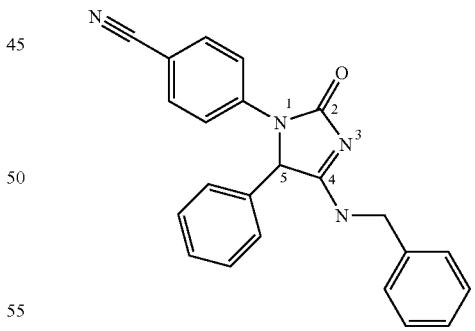

Similarly to compound 1,4-aminobenzonitrile, benzaldehyde and benzylisocyanide afforded the title compound as a brown solid (45 mg, 14%). $\delta_H$ NMR (CDCl$_3$, 300 MHz) 7.64 (2H, d, J=7.9 Hz, H arom), 7.48-7.39 (5H, m, H arom), 7.33-7.26 (5H, m, H arom), 7.16-7.12 (2H, m, H arom), 5.65 (1H, br signal, NH), 5.60 (1H, s, C$_5$H), 4.70 (1H, dd, J=14.8, 6.1 Hz, CH$_A$H$_B$Ph), 4.50 (1H, dd, J=14.7, 5.5 Hz, CH$_A$H$_B$Ph); m/z (EI) 337.2 (100%, M+H$^+$).

EXAMPLE 19

(Rac)-4-benzylamino-5-phenyl-1-(5-trifluoromethyl-pyridin-2-yl)-1,5-dihydro-imidazol-2-one

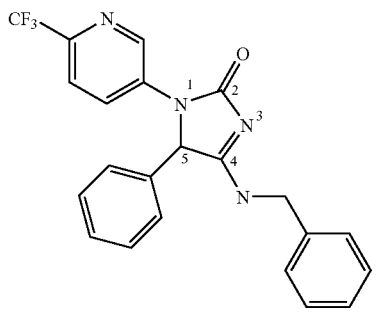

Similarly to compound 1,3-amino-6-(trifluoromethyl)pyridine, benzaldehyde and benzylisocyanide afforded the title compound as a black solid (31 mg, 9%). $\delta_H$ NMR (CDCl$_3$, 300 MHz) 8.52 (1H, dd, J=8.7, 2.4 Hz, H arom), 8.44 (1H, d, J=2.5 Hz, H arom), 7.56 (1H, d, J=8.7 Hz, H arom), 7.45-7.24 (8H, m, H arom), 7.15-7.09 (2H, m, H arom), 5.92 (1H, app t, J=5.3 Hz, NH), 5.67 (1H, s, C$_5$H), 4.68 (1H, dd, J=14.8, 6.1 Hz, CH$_A$H$_B$Ph), 4.49 (1H, dd, J=14.8, 5.5 Hz, CH$_A$H$_B$Ph); m/z (EI) 411.2 (100%, M+H$^+$).

EXAMPLE 20

(Rac)-4-benzylamino-1-(4-nitro-phenyl)-5-phenyl-1,5-dihydro-imidazol-2-one

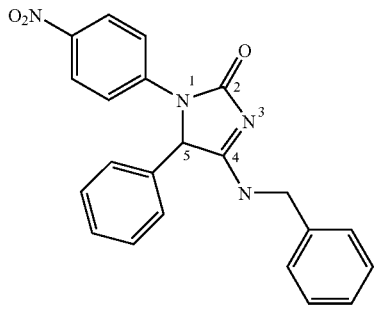

Similarly to compound 1,4-nitroaniline, benzaldehyde and benzylisocyanide afforded the title compound as a yellow oil (37 mg, 11%). $\delta_H$ NMR (CDCl$_3$, 300 MHz) 8.09 (1H, ddd, J=9.1, 3.1, 1.9 Hz, H arom), 7.70 (1H, ddd, J=9.4, 3.2, 2.2 Hz, H arom), 7.47-7.38 (4H, m, H arom), 7.36-7.14 (8H, m, H arom), 5.62 (1H, s, C$_5$H), 5.51 (1H, br signal, NH), 4.71 (1H, dd, J=14.8, 5.9 Hz, CH$_A$H$_B$Ph), 4.53 (1H, dd, J=14.8, 5.5 Hz, CH$_A$H$_B$Ph); m/z (EI) 387.2 (100%, M+H$^+$).

EXAMPLE 21

(Rac)-4-benzylamino-1-(3,4-dichloro-phenyl)-5-(3-methoxy-phenyl)-1,5-dihydro-imidazol-2-one

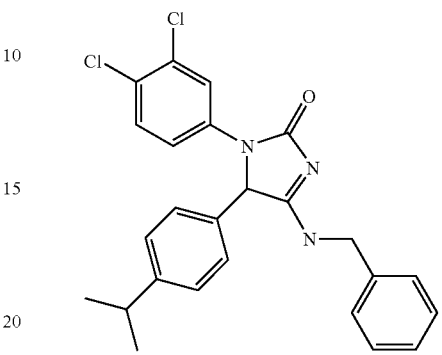

Similarly to compound 1, 3,4-dichloroaniline, p-isopropylbenzaldehyde and benzylisocyanide afforded the title compound as a white solid (47 mg, 12%). $\delta_H$ NMR (CDCl$_3$, 300 MHz) 7.75 (1H, d, J=2.2 Hz, H arom), 7.31-7.14 (11H, m, H arom), 5.49 (1H, s, C$_5$H), 5.32 (1H, br signal, NH), 4.73 (1H, dd, J=14.7, 6.1 Hz, CH$_A$CH$_B$Ph), 4.53 (1H, dd, J=14.8, 5.4 Hz, CH$_A$H$_B$Ph), 2.90 (1H, sept, J=6.7 Hz, CH(CH$_3$)$_2$), 1.27 (6H, d, J=7.0 Hz, 2×CH$_3$); m/z (EI) 454.3 (100%), 453.3 (38), 452.2 (94, M+H$^+$).

EXAMPLE 22

(Rac)-4-benzylamino-1-(3,4-dichloro-phenyl)-5-thiophen-3-yl-1,5-dihydroimidazol-2-one

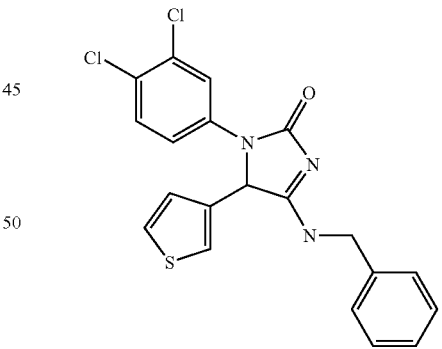

Similarly to compound 1, 3,4-dichloroaniline, 3-thiophene carboxaldehyde and benzylisocyanide afforded the title compound as light brown solid (18 mg, 5%). $\delta_H$ NMR (DMSO, 300 MHz) 8.87 (1H, app t, J=5.6 Hz, NHCH$_2$Ph), 7.94 (1H, d, J=2.1 Hz, H arom), 7.72 (1H, dd, J=2.8, 1.1 Hz, H thiophene), 7.54 (1H, dd, J=5.1, 3.0 Hz, H thiophene), 7.48-7.41 (2H, m, H arom), 7.33-7.18 (5H, m, H arom), 6.95 (1H, dd, J=5.1, 1.3 Hz, H thiophene), 6.27 (1H, s, C$_5$H), 4.49 (2H, d, J=5.6 Hz, CH$_2$Ph); m/z (EI) 419.2 (17%), 418.2 (61), 417.2 (21), 416.3 (100, M+H$^+$).

EXAMPLE 23

(Rac)-4-benzylamino-1-(3,4-difluoro-phenyl)-5-phenyl-1,5-dihydro-imidazol-2-one

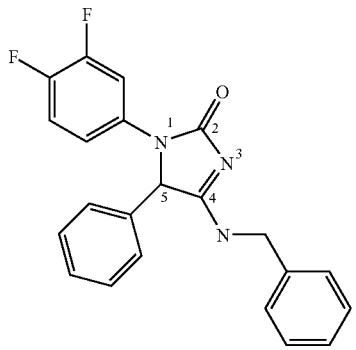

Similarly to compound 1, 3,4-difluoroaniline, benzaldehyde and benzylisocyanide afforded the title compound as an off-white solid (68 mg, 21%). $\delta_H$ NMR (CDCl$_3$, 300 MHz) 7.50 (1H, ddd, J=20.5, 7.0, 2.5 Hz, H arom), 7.44-7.35 (3H, m, H arom), 7.33-7.11 (7H, m, H arom), 6.96 (1H, dd, J=8.9, 8.7 Hz, H arom), 6.75 (1H, dd, J=9.0, 8.5 Hz, H arom), 5.51 (1H, s, C$_5$H), 5.47 (1H, app t, J=5.1 Hz, NH), 4.69 (1H, dd, J=14.7, 6.0 Hz, CH$_A$H$_B$Ph), 4.51 (1H, dd, J=14.7, 5.4 Hz, CH$_A$H$_B$Ph); m/z (EI) 378.3 (100%, M+H$^+$).

EXAMPLE 24

(Rac)-4-benzylamino-1-(3,4-dichloro-phenyl)-5-p-tolyl-1,5-dihydro-imidazol-2-one

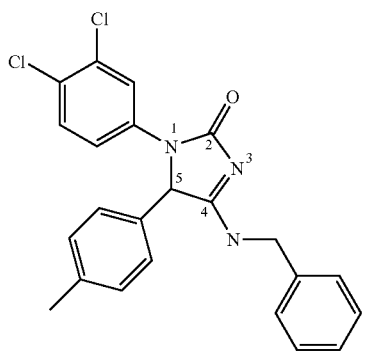

Similarly to compound 1, 3,4-dichloroaniline, p-tolylaldehyde and benzylisocyanide afforded the title compound as a white solid (9 mg, 3%). $\delta_H$ NMR (CDCl$_3$, 300 MHz) 7.72 (1H, d, J=2.3 Hz, H arom), 7.30-7.15 (11H, m, H arom), 5.45 (1H, s, C$_5$H), 5.37 (1H, br signal, NH), 4.72 (1H, dd, J=14.8, 6.2 Hz, CH$_A$CH$_B$Ph), 4.51 (1H, dd, J=14.5, 5.2 Hz, CH$_A$H$_B$Ph), 2.33 (3H, s, CH$_3$); m/z (EI) 427.2 (16%), 426.1 (52), 425.1 (22), 424.2 (100, M+H$^+$).

EXAMPLE 25

Rac-4-benzylamino-1-(3,4-dichloro-phenyl)-5-(3,4-dimethyl-phenyl)-1,5-dihydro-imidazol-2-one

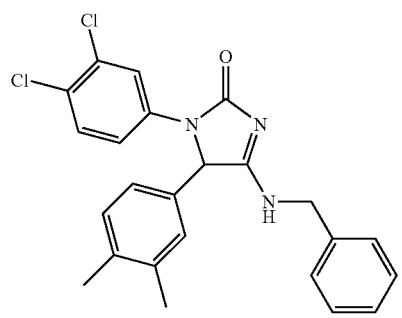

Similarly to compound 1, 3,4-dichloroaniline, 3,4-dimethylbenzaldehyde and benzylisocyanide afforded the title compound. (EI) 418.3 (M+H+)

EXAMPLE 26

(Rac)-4-benzylamino-1-(3,4-dichloro-phenyl)-5-(4-isopropyl-phenyl)-1,5-dihydro-imidazol-2-one

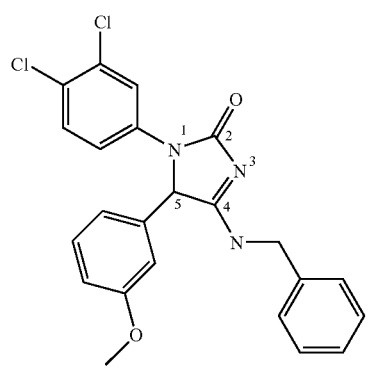

Similarly to compound 1, 3,4-dichloroaniline, m-anisaldehyde and benzylisocyanide afforded the title compound as a white solid (100 mg, 27%). $\delta_H$ NMR (DMSO, 300 MHz) 8.81 (1H, br signal, NH), 7.91 (1H, d, J=2.3 Hz, H arom), 7.47-7.38 (2H, m, 2H, arom), 7.32-7.17 (7H, m, H arom), 6.94 (2H, d, J=8.7 Hz, H arom), 6.10 (1H, s, C$_5$H), 4.46 (2H, br s, CH$_2$Ph), 3.72 (3H, s, OCH$_3$); m/z (EI) 444.3 (14%), 443.3 (14), 442.3 (62), 441.3 (22), 440.2 (100, M+H$^+$).

EXAMPLE 27

(Rac)-4-benzylamino-5-(4-chloro-phenyl)-1-(4-ethyl-phenyl)-1,5-dihydro-imidazol-2-one

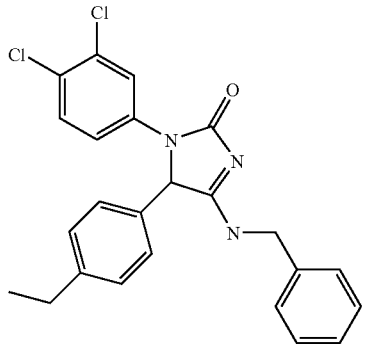

Similarly to compound 1, 3,4-dichloroaniline, p-ethylbenzaldehyde and benzylisocyanide afforded the title compound as a white solid (53 mg, 14%). $\delta_H$ NMR (CDCl$_3$, 300 MHz) 7.73 (1H, br s, H arom), 7.30-7.05 (11H, m, H arom), 5.49 (1H, s, C$_5$H), 5.30 (1H, br signal, NH), 4.73 (1H, dd, J=14.2, 5.1 Hz, CH$_A$CH$_B$Ph), 4.52 (1H, dd, J=14.5, 5.2 Hz, CH$_A$H$_B$Ph), 2.64 (2H, q, J=7.4 Hz, CH$_2$CH$_3$), 1.22 (3H, t, J=7.6 Hz, CH$_2$CH$_3$); m/z (EI) 440.2 (100%), 439.3 (30), 438.3 (60, M+H$^+$).

EXAMPLE 28

(Rac)-4-benzylamino-5-(4-chloro-phenyl)-1-(3,4-dichloro-phenyl)-1,5-dihydro-imidazol-2-one

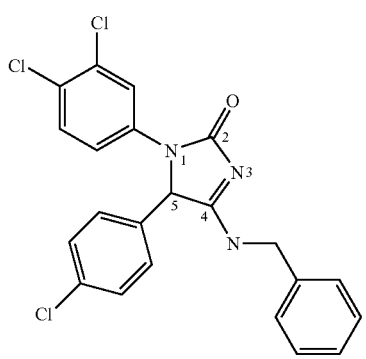

Similarly to compound 1, 3,4-dichloroaniline, 4-chlorobenzaldehyde and benzylisocyanide afforded the title compound as an off-white solid (16 mg, 4%). $\delta_H$ NMR (CDCl$_3$, 300 MHz) 7.68 (1H, s, H arom), 7.18-7.14 (11H, m, H arom), 5.50 (1H, s, C$_5$H), 5.29 (1H, br signal, NH), 4.74 (1H, dd, J=14.3, 5.9 Hz, CH$_A$CH$_B$Ph), 4.53 (1H, dd, J=14.3, 5.8 Hz, CH$_A$H$_B$Ph); m/z (EI) 446.1 (86%), 445.2 (28), 444.2 (100, M+H$^+$).

EXAMPLE 29 rac-4-Benzylamino-1-(3-chloro-4-fluoro-phenyl)-5-phenyl-1,5-dihydro-imidazol-2-one

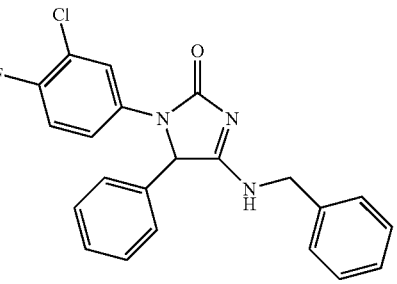

Similarly to example 1, reaction of benzaldehyde, benzyl isonitrile, and 3-chloro-4-fluoroaniline afforded the title compound. (EI) (M+H) 394.1

EXAMPLE 30

Rac-4-Benzylamino-1-(3-fluoro-phenyl-1,5-dihydro-imidazol-2-one

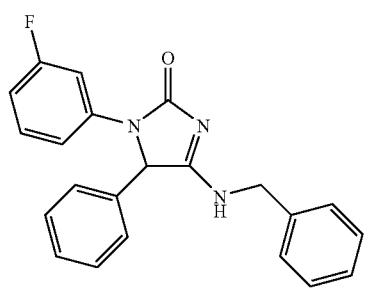

Similarly to example 1, reaction of benzaldehyde, benzyl isonitrile, and 3-fluoroaniline afforded the title compound. (EI) (M+H) 360.0

EXAMPLE 31

Rac-4-Benzylamino-1-(6-methoxy-pyridin-3-yl)-5-phenyl-1,5-dihydro-imidazol-2-one

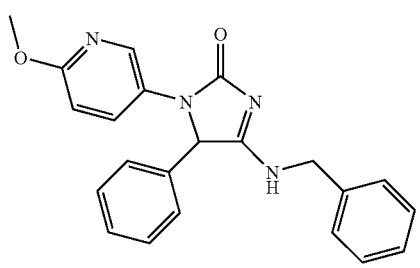

Similarly to example 1, reaction of benzaldehyde, benzyl isonitrile, and 5-amino-2-methoxypyridine afforded the title compound. (EI) (M+H) 373.3

EXAMPLE 32

Rac-4-Benzylamino-1-(3-fluoro-4-methyl-phenyl)-5-phenyl-1,5-dihydro-imidazol-2-one

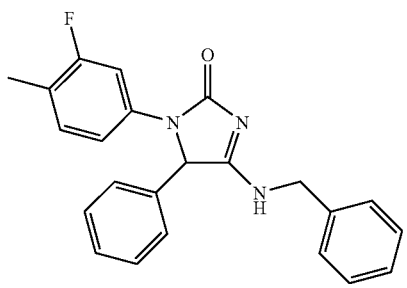

Similarly to example 1, reaction of benzaldehyde, benzyl isonitrile, and 3-fluoro-4-methylaniline afforded the title compound. (EI) (M+H) 374.4

EXAMPLE 33 rac-4-Benzylamino-1-(3,5-difluoro-phenyl)-5-phenyl-1,5-dihydro-imidazol-2-one

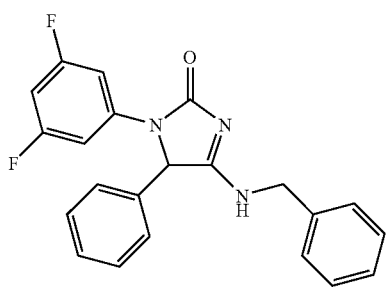

Similarly to example 1, reaction of benzaldehyde, benzyl isonitrile, and 3,5-difluoroaniline afforded the title compound. (EI) (M+H) 378.5

EXAMPLE 34 rac-4-Benzylamino-1-(6-chloro-pyridin-3-yl)-5-phenyl-1,5-dihydro-imidazol-2-one

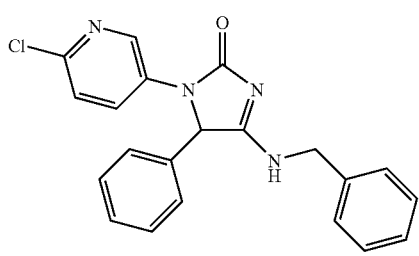

Similarly to example 1, reaction of benzaldehyde, benzyl isonitrile and 5-amino-2-chloropyridine afforded the title compound. (EI) (M−H) 375.3

EXAMPLE 35 rac-4-Benzylamino-5-phenyl-1-(4-trifluoromethoxy-phenyl)-1,5-dihydro-imidazol-2-one

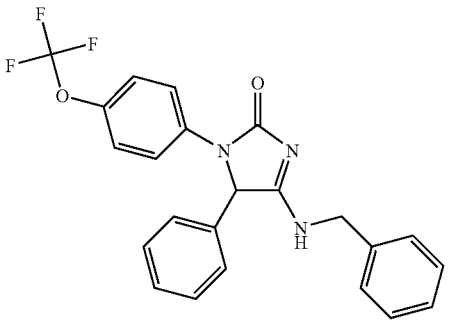

Similarly to example 1, reaction of benzaldehyde, benzyl isonitrile, and 4-(trifluoromethoxy)aniline afforded the title compound. (EI) (M+H) 426.1

EXAMPLE 36 rac-4-Benzylamino-5-phenyl-1-(3-trifluoromethyl-phenyl)-1,5-dihydro-imidazol-2-one

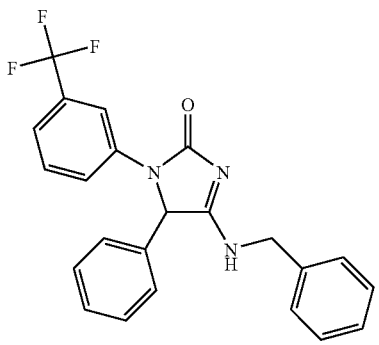

Similarly to example 1, reaction of benzaldehyde, benzyl isonitrile and 3-aminobenzotrifluoride afforded the title compound. (EI) (M+H) 410.4.

EXAMPLE 37

(Rac)-4-benzylamino-1-(3,4-dichloro-phenyl)-5-(2H-pyrazol-3-yl)-1,5-dihydroimidazol-2-one

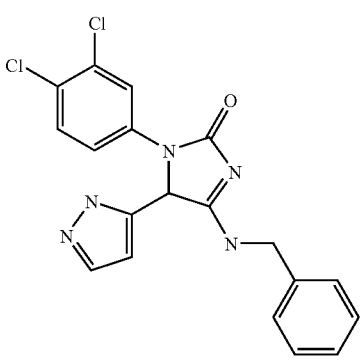

Similarly to compound 1, 3,4-dichloroaniline, 2H-pyrazole-3-carbaldehyde and benzylisocyanide afforded the title compound as an off-white solid (17 mg, 4%). $\delta_H$ NMR (DMSO, 300 MHz) 12.97 (1H, br s, NH pyrazole), 8.85 (1H, br signal, NHCH$_2$Ph), 7.91 (1H, s, H arom), 7.71 (1H, s, H arom), 7.48 (2H, s, H arom), 7.30-7.22 (5H, m, H arom), 6.19 (2H, s, H pyrazole+C$_5$H), 4.57-4.41 (2H, m, CH$_2$Ph); m/z (EI) 402.3 (71%), 401.2 (20), 400.2 (100, M+H$^+$).

EXAMPLE 38

(Rac)-4-benzylamino-1-(3,4-dichloro-phenyl)-5-pyridin-3-yl-1,5-dihydro-imidazol-2-one

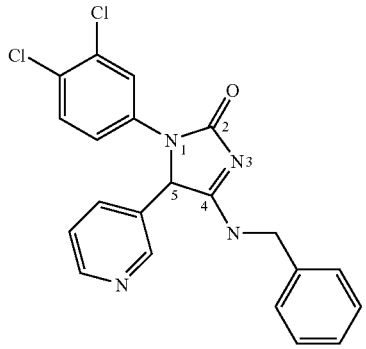

Similarly to compound 1, 3,4-dichloroaniline, 3-pyridine carboxaldehyde and benzylisocyanide afforded the title compound as an amber solid (36 mg, 10%). $\delta_H$ NMR (DMSO, 300 MHz) 9.03 (1H, br signal, NH), 8.71 (1H, d, J=1.9 Hz, H arom), 8.54 (1H, dd, J=4.8, 1.3 Hz, H arom), 7.94 (1H, d, J=2.3 Hz, H arom), 7.66 (1H, d, J=7.9H arom), 7.48-7.17 (8H, m, H arom), 6.28 (1H, s, C$_5$H), 4.48 (2H, s, CH$_2$Ph); m/z (EI) 413.2 (86%), 411.1 (100, M+H$^+$).

EXAMPLE 39

(Rac)-4-benzylamino-1-(3,4-dichloro-phenyl)-5-pyridin-4-yl-1,5-dihydro-imidazol-2-one

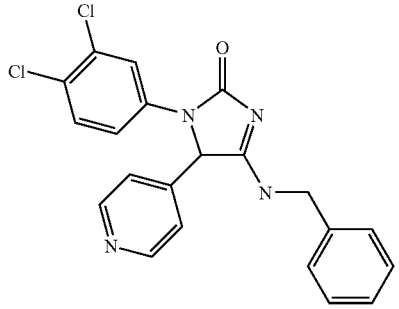

Similarly to compound 1, 3,4-dichloroaniline, 4-pyridine carboxaldehyde and benzylisocyanide afforded the title compound as a light yellow solid (21 mg, 6%). $\delta_H$ NMR (DMSO, 300 MHz) 9.01 (1H, br signal, NH), 8.59 (2H, d, J=5.2 Hz, H arom), 7.48-7.15 (9H, m, H arom), 6.26 (1H, s, C$_5$H), 4.47 (2H, s, CH$_2$Ph); m/z (EI) 414.3 (22%), 413.2 (85), 412.2 (23), 411.2 (100, M+H$^+$).

EXAMPLE 40

(Rac)-4-benzylamino-1-(3,4-dichloro-phenyl)-5-furan-2-yl-1,5-dihydro-imidazol-2-one

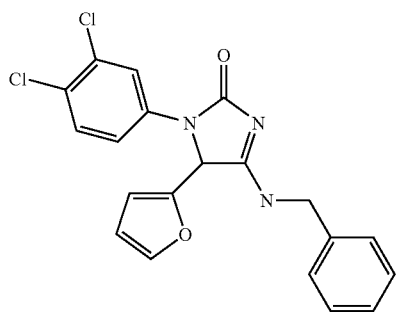

Similarly to compound 1, 3,4-dichloroaniline, 2-furaldehyde and benzylisocyanide afforded the title compound as an amber solid (22 mg, 7%). $\delta_H$ NMR (DMSO, 300 MHz) 9.04 (1H, app t, J=5.6 Hz, NH), 7.91 (1H, d, J=1.1 Hz, H arom), 7.65 (1H, d, J=1.0 Hz, H arom), 7.50 (2H, s, H arom), 7.35-7.22 (5H, m, H arom), 6.73 (1H, d, J=3.2 Hz, H furane), 6.46 (1H, dd, J=3.2, 1.9 Hz, H furane), 6.38 (1H, s, C$_5$H), 4.55 (1H, dd, J=15.7, 6.4 Hz, CH$_A$H$_B$Ph), 4.49 (1H, dd, J=15.3, 6.0 Hz, CH$_A$H$_B$Ph); m/z (EI) 403.3 (15%), 402.3 (74), 401.1 (29), 400.1 (100, M+H$^+$).

EXAMPLE 41

(Rac)-4-benzylamino-1-(3,4-dichloro-phenyl)-5-(3-methoxy-phenyl)-1,5-dihydro-imidazol-2-one

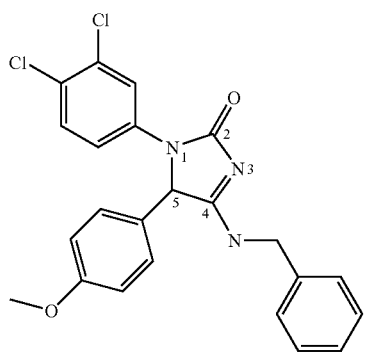

Similarly to compound 1, 3,4-dichloroaniline, p-anisaldehyde and benzylisocyanide afforded the title compound as a white solid (52 mg, 14%). $\delta_H$ NMR (CDCl$_3$, 300 MHz) 7.75 (1H, d, J=2.3 Hz, H arom), 7.36-7.16 (8H, m, H arom), 6.92-6.87 (2H, m, H arom), 6.75 (1H, s, H arom), 5.47 (1H, s, C$_5$H), 5.36 (1H, app t, J=4.4 Hz, NH), 4.72 (1H, dd, J=14.8, 5.9 Hz, CH$_A$CH$_B$Ph), 4.53 (1H, dd, J=14.9, 5.6 Hz, CH$_A$H$_B$Ph), 3.76 (3H, s, OCH3); m/z (EI) 442.3 (56%), 441.3 (19), 440.2 (100, M+H$^+$).

EXAMPLE 42

(Rac)-4-benzylamino-1-(3,4-dichloro-phenyl)-5-(4-dimethylamino-phenyl)-1,5-dihydro-imidazol-2-one

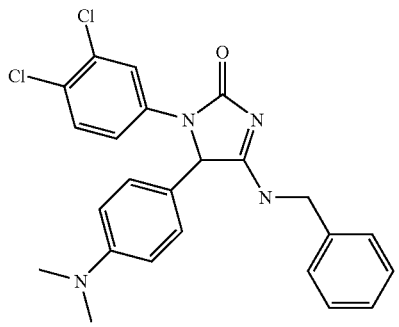

Similarly to compound 1, 3,4-dichloroaniline, 4-(dimethylamino)benzaldehyde and benzylisocyanide afforded the title compound as a gold solid (36 mg, 9%). δ$_H$ NMR (DMSO, 300 MHz) 8.82 (1H, app t, J=5.6 Hz, NH), 7.90 (1H, d, J=1.7 Hz, H arom), 7.46-7.38 (2H, m, H arom), 7.31-7.11 (7H, m, H arom), 6.68 (2H, d, J=8.5 Hz, H arom), 6.00 (1H, s, C$_5$H), 4.46 (2H, d, J=5.7 Hz, CH$_2$Ph), 2.86 (6H, s, N(CH$_3$)$_2$); m/z (EI) 456.4 (19%), 455.3 (74), 454.3 (29), 453.3 (100, M+H$^+$).

EXAMPLE 43

(Rac)-4-benzylamino-1-(3,4-dichloro-phenyl)-5-(4-fluoro-phenyl)-1,5-dihydro-imidazol-2-one

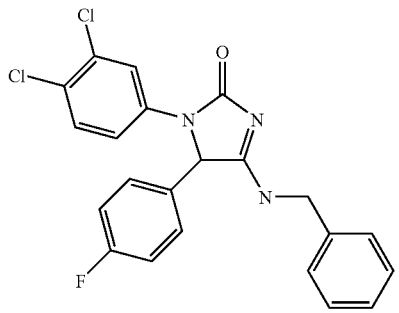

Similarly to compound 1, 3,4-dichloroaniline, 4-fluorobenzaldehyde and benzylisocyanide afforded the title compound as a white solid (72 mg, 20%). δ$_H$ NMR (DMSO, 300 MHz) 8.89 (1H, app t, J=5.8 Hz, NH), 7.92 (1H, d, J=2.3 Hz, H arom), 7.47-7.38 (4H, m, H arom), 7.30-7.16 (7H, m, H arom); 6.21 (1H, s, C$_5$H), 4.47 (2H, d, J=5.6 Hz, CH$_2$Ph); m/z (EI) 431.2 (16%), 430.3 (59), 429.3 (23), 428.3 (100, M+H$^+$).

EXAMPLE 44

Rac-4-Benzylamino-1-(3-chloro-4-fluoro-phenyl)-5-(4-fluoro-phenyl)-1,5-dihydro-imidazol-2-one

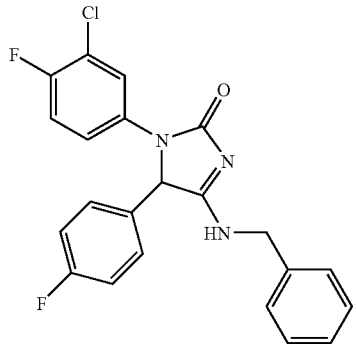

Similarly to example 1, reaction 4-fluorobenzaldehyde and 3-chloro-4-fluorobenzylamine and Benzyl isonitrile afforded the title compound. (EI) (M–H) 375.31; H NMR (DMSO, 300 MHz) 8.84 (1H, app t, J=5.8 Hz, NH), 7.84 (1H, dd, J=6.6, 2.1 Hz, H arom), 7.43-7.36 (4H, m, H arom), 7.32-7.16 (7H, m, H arom), 6.19 (1H, s, CH), 4.47 (2H, d, J=5.7 Hz, CH2Ph; m/z (EI) 412.2 (M+H+).

EXAMPLE 45

(Rac)-4-benzylamino-1-(3,4-dichloro-phenyl)-5-thiophen-2-yl-1,5-dihydroimidazol-2-one

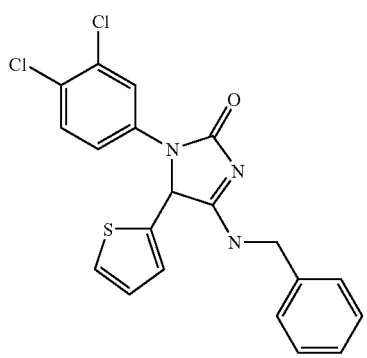

Similarly to compound 1, 3,4-dichloroaniline, 2-thiophene carboxaldehyde and benzylisocyanide afforded the title compound as a brown solid (7 mg, 2%). δ$_H$ NMR (DMSO, 300 MHz) 9.00 (1H, app t, J=5.9 Hz, NHCH$_2$Ph), 7.90 (1H, d, J=2.1 Hz, H arom), 7.53 (1H, d, J=5.1 Hz, H thiophene), 7.50-7.47 (2H, m, H arom), 7.42 (1H, dd, J=3.6, 1.1 Hz, H thiophene), 7.34-7.20 (5H, m, H arom), 7.03 (1H, dd, J=5.0, 3.5 Hz, H thiophene), 6.57 (1H, s, C$_5$H), 4.51 (1H, d, J=5.4 Hz, CH$_A$CH$_B$Ph), 4.49 (1H, dd, J=5.5 Hz, CH$_A$H$_B$Ph); m/z (EI) 419.1 (18%), 418.2 (63), 417.2 (21), 416.2 (100, M+H$^+$).

EXAMPLE 46

Rac-4-Benzylamino-1-(4-fluoro-phenyl)-5-phenyl-1,5-dihydro-imidazol-2-one

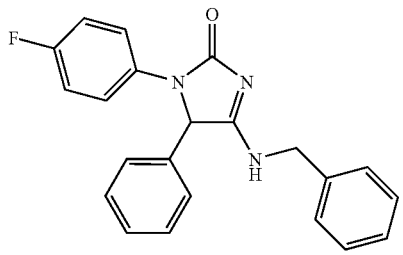

Similarly to example 1, reaction of benzaldehyde, benzyl isonitrile and 4-fluoroaniline afforded the title compound. (EI) (M+H) 360.4.

EXAMPLE 47 rac-4-Benzylamino-1-(4-morpholin-4-yl-phenyl)-5-phenyl-1,5-dihydro-imidazol-2-one

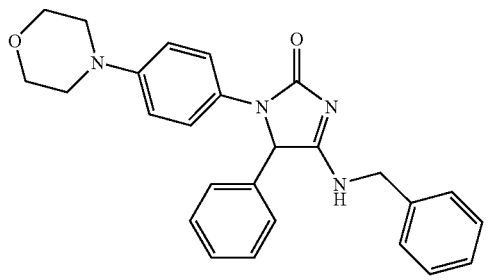

Similarly to example 1, reaction of benzaldehyde, benzyl isonitrile and 4-morpholinoaniline afforded the title compound. (EI) (M+H) 427.5.

EXAMPLE 48 rac-1-(3,4-Dichloro-phenyl)-4-[2-(3,4-dimethoxy-phenyl)-ethylamino]-5-phenyl-1,5-dihydro-imidazol-2-one

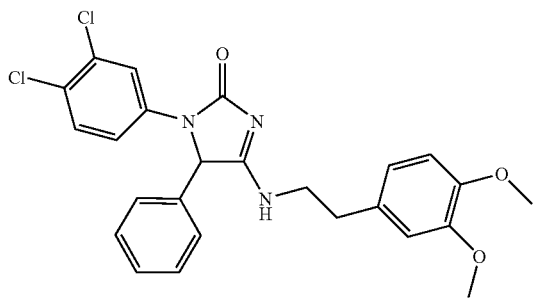

Similarly to example 1, reaction of benzaldehyde, 4-(2-isocyano-ethyl)-1,2-dimethoxy-benzene and, 4-dichloroaniline afforded the title compound. (EI) (M+H) 484.5.

EXAMPLE 49 AND EXAMPLE 50

(+)-4-Benzylamino-1-(4-chloro-phenyl)-5-phenyl-1,5-dihydro-imidazol-2-one and (−)-4-Benzylamino-1-(4-chloro-phenyl)-5-phenyl-1,5-dihydro-imidazol-2-one

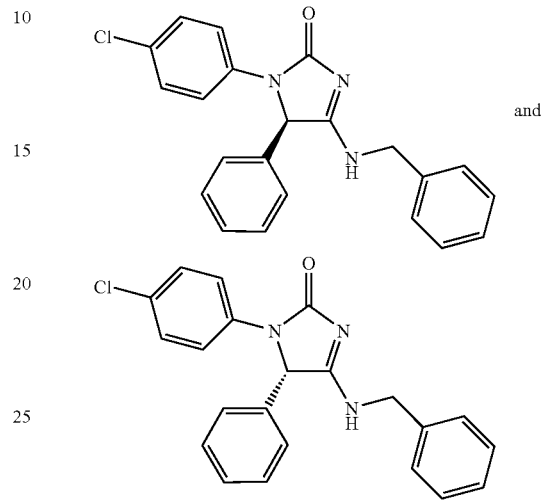

A chiral chromatography of example 10 on Chiralpak AD eluting with heptane-isopropanole 4:1, chiral separated both enantiomers (Example 49 and 50). Mass spectra of Example 49 showed mass peak of 376.4 (M+H) and that of Example 50 showed 376.5 (M+H).

EXAMPLE 51

Rac-1-(3,4-dichloro-phenyl)-4-(4-fluorobenzylamino)-5-phenyl-1,5-dihydro-imidazol-2-one Step 1: 1-(3,4-Dichloro-phenyl)-5-phenyl-1,3-dihydro-imidazol-2-one

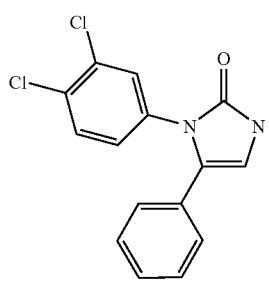

250 mL of concentrated HCl were added 1-(3,4-dichlorophenyl)-3-(2-oxo-2-phenyl-ethyl)urea (1 equiv., 56 mmol, 18.0 g) at room temperature. The reaction mixture was stirred for one week until starting material disappeared giving a white foam which was filtered off. This foam was purified by recrystallization in ethanol affording 1-(3,4-dichloro-phenyl)-5-phenyl-1,3-dihydro-imidazol-2-one (14.4 g, 85%) as a white solid. $R_f$ 0.2 (n-heptane/ethyl acetate 2:1). $\delta_H$ NMR (DMSO, 300 MHz) 10.68 (1H, br s, NH), 7.62 (1H, d, J=8.6 Hz, H arom), 7.53 (1H, d, J=2.4 Hz, H arom), 7.32-7.20 (3H, m, H arom), 7.09-7.06 (2H, m, H arom), 7.03 (1H, dd, J=8.6, 2.5 Hz, H arom), 6.89 (1H, s, =CH); m/z (EI) 309.2 (21%), 307.2 (97), 306.1 (24), 305.1 (100, M+H+).

Step 2: Rac-1-(3,4-dichloro-phenyl)-4-(4-fluorobenzylamino)-5-phenyl-1,5-dihydro-imidazol-2-one

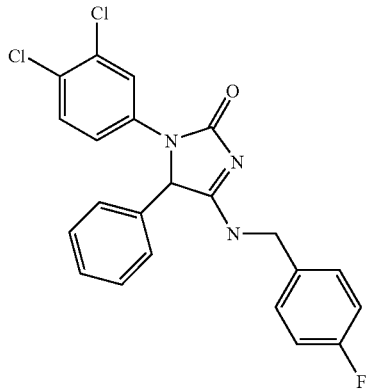

To a stirred solution of 1-(3,4-dichloro-phenyl)-5-phenyl-1,3-dihydro-imidazol-2-one (1 equiv., 0.33 mmol, 100 mg) in chloroform (5 mL) was added dropwise Br$_2$ (1.1 equiv., 0.36 mmol, 19 μL) in chloroform (2 mL) at 0° C. under nitrogen. After 10 min, 4-fluorobenzylamine (10 equiv., 3.28 mmol, 372 μL) was added in situ at 0° C. The reaction mixture was allowed to warm up to room temperature and heated at reflux overnight. After evaporation of solvent, the residue was purified by column chromatography (SiO$_2$, n-heptane/ethyl acetate: 0-100%) affording the title compound as a white solid (32 mg, 23%). δ$_H$ NMR (DMSO, 300 MHz) 8.83 (1H, br, s, NH), 7.91 (1H, d, J=2.4 Hz, H arom), 7.46-7.08 (11H, m, H arom), 6.16 (1H, s, C$_5$H), 4.44 (2H, s, CH$_2$Ph); m/z (EI) 431.0 (12%), 430.0 (74), 429.1 (26), 428.0 (100, M+H+).

EXAMPLE 52

Rac-1-(3,4-dichloro-phenyl)-4-isobutylamino-5-phenyl-1,5-dihydroimidazol-2-one

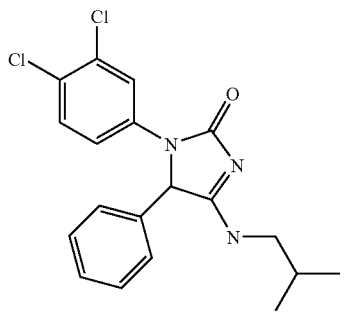

Similarly to compound 51, isopropylamine afforded the title compound as a white solid (88 mg, 71%). δ$_H$ NMR (DMSO, 300 MHz) 8.34 (1H, app t, J=5.6 Hz, NH), 7.92 (1H, d, J=2.1 Hz, H arom), 7.42-7.31 (7H, m, H arom), 6.06 (1H, s, C$_5$H), 3.17-3.08 (1H, m, NH—CH$_A$H$_B$-iPr), 3.03-2.97 (1H, m, NH—CH$_A$H$_B$-iPr), 1.80 (1H, non, J=6.7 Hz, CH(CH$_3$)$_2$), 0.74 (3H, d, J=6.6 Hz, CH$_3$), 0.71 (3H, d, J=6.8 Hz, CH$_3$); m/z (EI) 379.2 (13%), 378.2 (65), 377.3 (22), 376.3 (100, M+H+).

EXAMPLE 53

Rac-1-(3,4-dichloro-phenyl)-4-(3-methyl-butylamino)-5-phenyl-1,5-dihydoimidazol-2-one

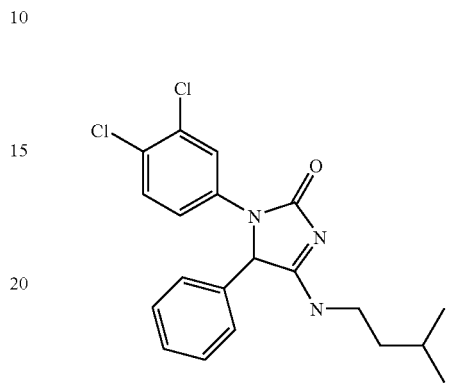

Similarly to compound 51, isoamylamine afforded the title compound as a white solid (52 mg, 41%). δ$_H$ NMR (DMSO, 300 MHz) 8.28 (1H, br signal, NH), 7.91 (1H, d, J=2.1 Hz, H arom), 7.45-7.30 (7H, m, H arom), 6.05 (1H, s, C$_5$H), 3.25 (2H, br t, J=6.9 Hz, NH—CH$_2$), 1.43 (1H, non, J=6.0 Hz, CH(CH$_3$)$_2$), 1.36-1.29 (2H, m, CH$_2$CH(CH$_3$)$_2$), 0.81 (6H, d, J=6.4 Hz, 2×CH$_3$); m/z (EI) 393.2 (15%), 392.2 (66), 391.1 (19), 390.2 (100, M+H+).

EXAMPLE 54

(Rac)-1-(3,4-dichloro-phenyl)-5-phenyl-4-[(pyridin-4-ylmethyl)-amino]-1,5-dihydro-imidazol-2-one

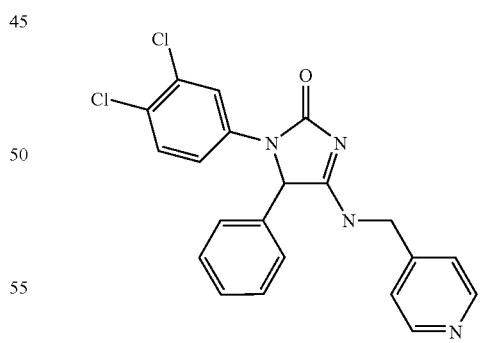

Similarly to compound 51, 4-aminomethyl)pyridine afforded the title compound as an off-white solid (23 mg, 17%) δ$_H$ NMR (DMSO, 300 MHz) 8.83 (1H, br signal, NH), 8.46 (2H, d, J=6.0 Hz, H pyridine), 7.92 (1H, d, J=2.2 Hz, H arom), 7.47-7.33 (7H, m, H arom), 7.12 (2H, d, J=5.9 Hz, H pyridine), 6.23 (1H, s, C$_5$H), 4.48 (2H s, CH$_2$Ph); m/z (EI) 413.0 (30%), 411.0 (52, M+H+), 200.2 (100)

EXAMPLE 55 rac-1-(3,4-Dichloro-phenyl)-4-(methyl-propyl-amino)-5-phenyl-1,5-dihydro-imidazol-2-one

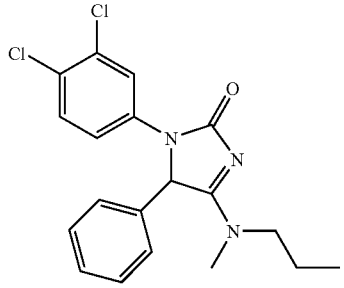

Similarly to compound 51, N,N-methylpropylamine afforded the title compound. (EI) 376.3 (M+H+)

EXAMPLE 56

(Rac)-4-azepan-1-yl-1-(3,4-dichloro-phenyl)-5-phenyl-1,5-dihydro-imidazol-2-one

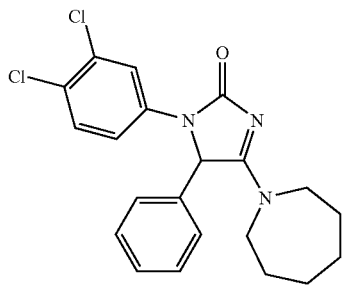

Similarly to compound 51, hexamethyleneimine afforded the title compound as a white solid (65 mg, 49%). $\delta_H$ NMR (DMSO, 300 MHz) 7.49 (1H, d, J=2.4 Hz, H arom), 7.56-7.28 (7H, m, H arom), 6.47 (1H, s, C$_5$H), 3.78-3.71 (2H, m, CH$_2$), 3.36-3.33 (4H, m, 2×CH$_2$), 1.56-1.45 (4H, m, 2×CH$_2$), 1.32-1.13 (2H, m, CH$_2$); m/z (EI) 405.2 (16%), 404.2 (78), 403.2 (24), 402.1 (100, M+H$^+$), 200.1 (59).

EXAMPLE 57

(Rac)-1-(3,4-dichloro-phenyl)-4-hexylamino-5-phenyl-1,5-dihydro-imidazol-2-one

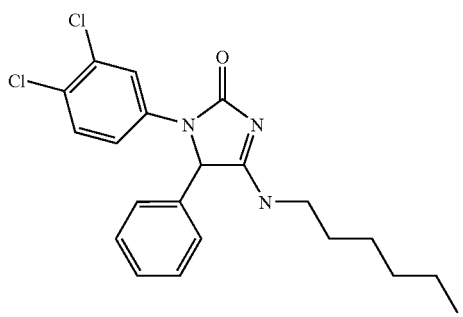

Similarly to compound 51, hexylamine afforded the title compound as a white solid (57 mg, 49%). $\delta_H$ NMR (DMSO, 300 MHz) 8.30 (1H, app t, J=5.7 Hz, NH), 7.92 (1H, d, J=2.1 Hz, H arom), 7.45-7.28 (7H, m, H arom), 6.05 (1H, s, C$_5$H), 3.25 (1H, d, J=5.4 Hz, NH—CH$_A$H$_B$), 3.21 (1H, d, J=5.4 Hz, NH—CH$_A$H$_B$), 1.42 (2H, qt, J=6.7 Hz, NH—CH$_2$—CH$_2$), 1.23-1.07 (6H, m, CH$_2$—CH$_2$—CH$_2$—CH$_3$), 0.81 (3H, t, J=6.5 Hz, CH$_3$); m/z (EI) 406.2 (49%), 405.1 (22), 404.2 (100, M+H$^+$), 200.1 (87).

EXAMPLE 58

(Rac)-4-(cyclohexylmethyl-amino)-1-(3,4-dichloro-phenyl)-5-phenyl-1,5-dihydro-imidazol-2-one

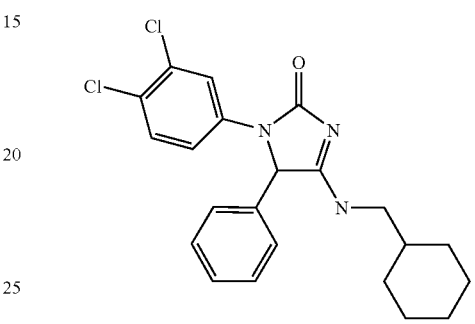

Similarly to compound 51, (aminomethyl)cyclohexane afforded the title compound as an off-white solid (41 mg, 30%). $\delta_H$ NMR (DMSO, 300 MHz) 8.31 (1H, app t, J=5.6 Hz, NH), 7.92 (1H, d, J=2.3 Hz, H arom), 7.45-7.31 (7H, m, H arom), 6.06 (1H, s, C$_5$H), 3.14-3.03 (2H, m, NH—CH$_2$—Cy), 1.59-1.44 (6H, m, 3×CH$_2$), 1.11-1.04 (3H, m, CH+CH$_2$), 0.80-0.60 (2H, m, CH$_2$); m/z (EI) 419.1 (16%), 418.1 (64), 417.1 (26), 416.1 (100, M+H$^+$), 200.2 (34).

EXAMPLE 59

(Rac)-4-butylamino-1-(3,4-dichloro-phenyl)-5-phenyl-1,5-dihydro-imidazol-2-one

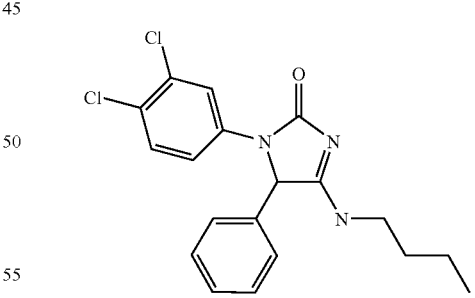

Similarly to compound 51, n-butylamine afforded the title compound as a white solid (18 mg, 15%). $\delta_H$ NMR (DMSO, 300 MHz) 8.30 (1H, app t, 1=5.5 Hz, NH), 7.92 (1H, d, J=2.1 Hz, H arom), 7.45-7.29 (7H, m, H arom), 6.05 (1H, s, C$_5$H), 3.26 (1H, d, J=6.6 Hz, NH—CH$_A$H$_B$), 3.21 (1H, d, J=6.8 Hz, NH—CH$_A$H$_B$), 1.42 (2H, qt, J=7.4 Hz, NH—CH$_2$—CH$_2$), 1.16 (2H, sext, J=7.5 Hz, CH$_2$—CH$_2$—CH$_3$), 0.81 (3H, t, J=7.4 Hz, CH$_3$); m/z (EI) 378.1 (47%), 376.1 (68, M+H$^+$), 200.1 (100).

EXAMPLE 60

(Rac)-4-(cyclopropylmethyl-amino)-1-(3,4-dichloro-phenyl)-5-phenyl-1,5-dihydro-imidazol-2-oe

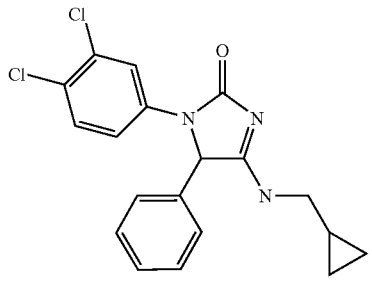

Similarly to compound 51, aminomethylcyclopropane afforded the title compound as a light brown solid (31 mg, 25%). $\delta_H$ NMR (DMSO, 300 MHz) 8.44 (1H, app t, J=4.8 Hz, NH), 7.91 (1H, br s, H arom), 7.45-7.21 (7H, m, H arom), 6.07 (1H, s, C$_5$H), 3.25-3.16 (1H, m, NH—CH$_A$H$_B$), 3.10-3.01 (1H, m, NH—CH$_A$H$_B$), 0.97 (1H, br sept, J=8.3 Hz, CH), 0.37 (2H, br d, J=7.7 Hz, CH$_2$), 0.16 (2H, br d, J=3.5 Hz, CH$_2$); m/z (EI) 377.2 (15%), 376.1 (75), 375.1 (16), 373.9 (100, M+H$^+$).

EXAMPLE 61 rac-1-(3,4-Dichloro-phenyl)-4-dimethylamino-5-phenyl-1,5-dihydro-imidazol-2-one

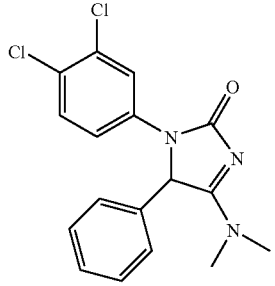

Similarly to compound 51, N,N-dimethylamine afforded the title compound. (EI) 348.2 (M+H+)

EXAMPLE 62 rac-1-(3,4-Dichloro-phenyl)-4-methylamino-5-phenyl-1,5-dihydro-imidazol-2-one

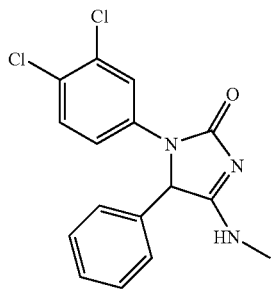

Similarly to compound 51, N-methylamine afforded the title compound. (EI) 334.0 (M+H+)

EXAMPLE 63 rac-4-Cyclobutylamino-1-(3,4-dichloro-phenyl)-5-phenyl-1,5-dihydro-imidazol-2-one

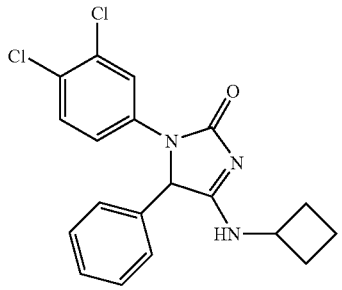

Similarly to compound 51, cyclopropylamine afforded the title compound. (EI) 373.9 (M+H+)

EXAMPLE 64 rac-1-(3,4-Dichloro-phenyl)-4-(3,4-dihydro-1H-iso-quinolin-2-yl)-5-phenyl-1,5-dihydro-imidazol-2-one

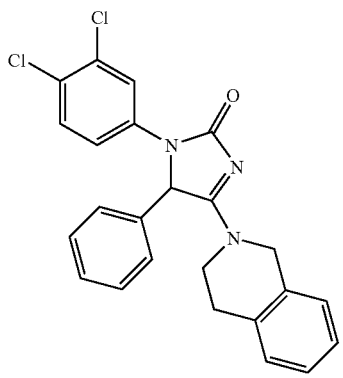

Similarly to compound 51, 1,2,3,4-tetrahydroquinoline afforded the title compound. (EI) 436.0 (M+H+).

EXAMPLE 65 rac-4-Cyclopentylamino-1-(3,4-dichloro-phenyl)-5-phenyl-1,5-dihydro-imidazol-2-one

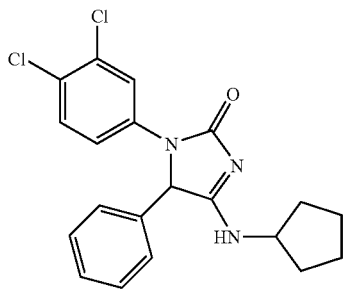

41

Similarly to compound 51, cyclopentylamine afforded the title compound. (EI) 388.1 (M+H+)

EXAMPLE 66

Rac-1-(4-Chloro-phenyl)-4-isobutylamino-5-phenyl-1,5-dihydro-imidazol-2-one

Step 1: Synthesis of 1-(2-oxo-phenyl-ethyl)ureas

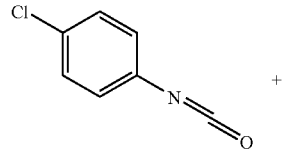

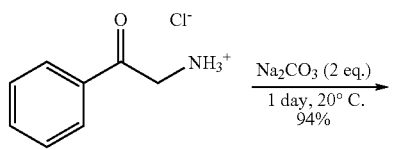

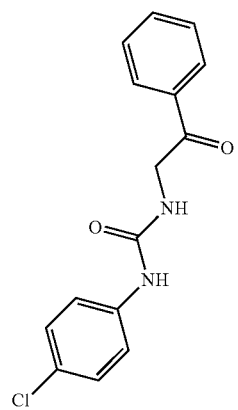

To a suspension of 1-chloro-4-isocyanato-benzene (0.033 mol) and 2-oxo-2-phenyl-ethyl-ammonium chloride (0.033 mol, 1 eq.) was added an aqueous solution of sodium carbonate ([1.3], 50 ml, 0.065 mol, 2 eq.). The reaction mixture was stirred overnight at room temperature affording a white precipitate which was filtered off. The precipitate was dissolved in dichloromethane (10 mL), dried over $Na_2S_2O_4$, and concentrated in vacuo affording the solid product. The product was dried under high vacuum at 60° C. for 4 hours.

Step 2: Synthesis of 1,5-Diphenyl-1,3-dihydro-imidazol-2-ones

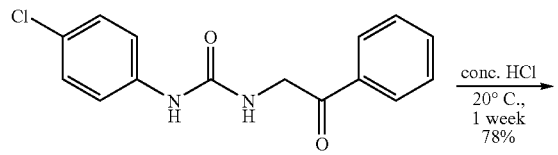

42

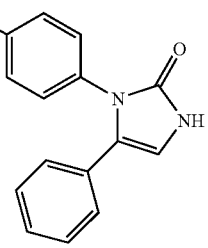

10 mL of concentrated hydrochloric acid (fuming 37%) was added to 1-(4-chloro-phenyl)-3-(2-oxo-2-phenyl-ethyl)-urea (0.017 mol) to form a suspension at room temperature. The reaction mixture was stirred for one week until the suspension had transformed into a white foam corresponding to the desired product by LC-MS which was filtered off.

Step 3: Amination of 1,5-Diphenyl-1,3-dihydro-imidazol-2-ones

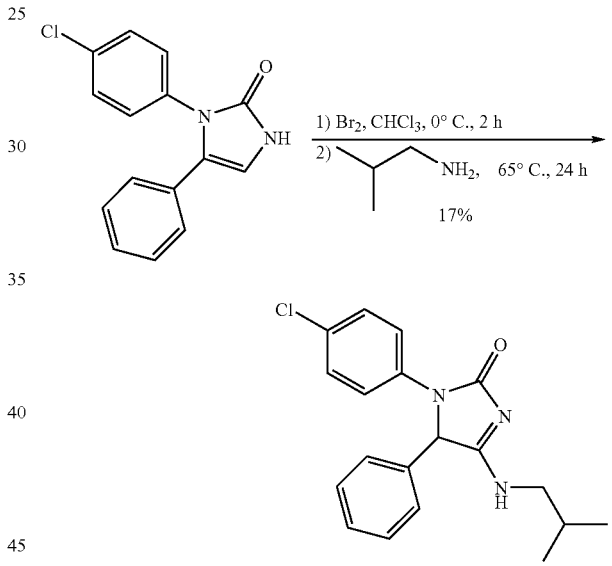

To a solution of 1-(4-chloro-phenyl)-5-phenyl-1,3-dihydro-imidazol-2-one (0.37 mmol) in dry chloroform (3 mL) in the presence of molecular sieves (4 Å), a solution of bromine (3 mL, [0.13M] in chloroform) was added dropwise using a syringe. The reaction mixture was stirred at 0° C. until completion of bromination was observed by TLC. Isobutylamine (1.8 mmol, 5 eq.) was then added via a syringe and the reaction was allowed to warm to room temperature and was then heated to 65° C. for 24 hours. The reaction was carried under nitrogen throughout. The product was concentrated at reduced pressure and purified by column (amine functionalised $SiO_2$, heptane: ethylacetate=0-100%).

m/z (CI+) 705.2 (22%), 683.5 (35), 364.1 (29), 343.2 (22), 342.2 (100% M+H+) $□_H$NMR (DMSO, 300 MHz)=8.22 (1H, m, pos Rb1, NH), 7.54-7.52 (2H, d, J=8.5 Hz, pos Ra3,5, H arom), 7.44-7.20 (5H, m, pos Rc, H arom), 7.25-7.22 (2H, d, J=8.5 Hz, pos Ra2,6, H arom), 6.01 (1H, s, pos 5, H alkyl), 3.14-2.99 (2H, m, pos Rb2, H alkyl), 1.80-1.76 (1H, m, pos Rb3, H alkyl), 0.75-0.70 (6H, m, pos Rb4,5, H alkyl)

EXAMPLE 67

1-(3,4-Difluoro-phenyl)-4-isobutylamino-5-phenyl-1,5-dihydro-imidazol-2-one

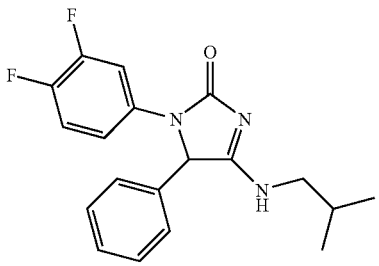

Similarly to Example 66, the title compound was prepared from 1,2-difluoro-4-isocyanato-benzene.

m/z (CI$^+$) 709.5 (54%), 687.3 (51), 366.1 (49), 345.2 (21), 344.1 (100% M+H$^+$) $\square_H$NMR (DMSO, 300 MHz)=8.3-8.27 (1H, t, J=6.0 Hz, pos Rb1, NH), 7.75-7.67 (1H, t, d, J=7.5, 3.0 Hz, pos Ra2H arom), 7.41-7.17 (7H, m, H arom), 6.02 (1H, s, pos 5, H alkyl), 3.17-2.95 (2H, dd, pos Rb2, H alkyl), 1.85-1.73 (1H, m, pos Rb3, H alkyl), 0.75-0.70 (6H, m, pos Rb4,5, H alkyl)

What is claimed is:
1. A compound of formula I

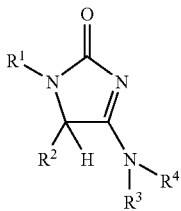

wherein
 R$^1$ is —(CH$_2$)$_n$-aryl or —(CH$_2$)$_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
 R$^2$ is —(CH$_2$)$_n$-aryl or —(CH$_2$)$_n$-heteroaryl, wherein such groups are unsubstituted or substituted by one or more substituents selected from the group consisting of lower alkyl, lower alkoxy, halogen and —N(lower alkyl)$_2$;
 R$^3$ is hydrogen or lower alkyl;
 R$^4$ is —(CH$_2$)$_n$-aryl or —(CH$_2$)$_n$-heteroaryl, wherein such groups are unsubstituted or substituted by one or more substituents selected from the group consisting of halogen and lower alkoxy, or is lower alkyl; or
 R$^3$ and R$^4$ form together with the N-atom to which they are attached a heterocyclic ring; and
 n is 0, 1 or 2;
 or a pharmaceutically acceptable acid addition salt thereof.

2. A compound of claim 1 having formula IA

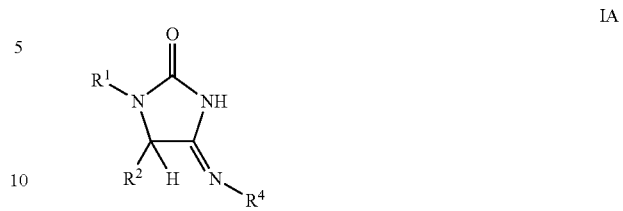

wherein
 R$^1$ is —(CH$_2$)$_n$-aryl or —(CH$_2$)$_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
 R$^2$ is —(CH$_2$)$_n$-aryl or —(CH$_2$)$_n$-heteroaryl, wherein such groups are unsubstituted or substituted by one or more substituents selected from the group consisting of lower alkyl, lower alkoxy, halogen and —N(lower alkyl)$_2$;
 R$^4$ is —(CH$_2$)$_n$-aryl or —(CH$_2$)$_n$-heteroaryl, wherein such groups are unsubstituted or substituted by one or more substituents selected from the group consisting of halogen and lower alkoxy, or is lower alkyl, and
 n is 0, 1 or 2;
 or a pharmaceutically acceptable acid addition salt thereof.

3. A compound of claim 1, wherein R$^1$ is phenyl substituted by halogen, R$^2$ is phenyl and R$^4$ is benzyl.

4. A compound of claim 3, selected from the group consisting of
 (Rac)-4-benzylamino-1-(4-chloro-phenyl)-5-phenyl-1,5-dihydro-imidazol-2-one
 (Rac)-4-benzylamino-1-(3,4-dichloro-phenyl)-5-phenyl-1,5-dihydro-imidazol-2-one and
 (−)-4-benzylamino-1-(4-chloro-phenyl)-5-phenyl-1,5-dihydro-imidazol-2-one.

5. A compound of claim 1, wherein R$^1$ is phenyl substituted by halogen, R$^2$ is phenyl substituted by lower alkyl and R$^4$ is benzyl.

6. A compound of claim 5, selected from the group consisting of
 (Rac)-4-benzylamino-1-(3,4-dichloro-phenyl)-5-p-tolyl-1,5-dihydro-imidazol-2-one and
 (Rac)-4-benzylamino-1-(3,4-dichloro-phenyl)-5-(3,4-dimethyl-phenyl)-1,5-dihydro-imidazol-2-one.

7. A compound of claim 1, wherein R$^1$ and R$^2$ are phenyl substituted by halogen and R$^4$ is benzyl.

8. A compound of claim 7, selected from the group consisting of
 (Rac)-4-benzylamino-5-(4-chloro-phenyl)-1-(3,4-dichloro-phenyl)-1,5-dihydro-imidazol-2-one
 (Rac)-4-benzylamino-1-(3,4-dichloro-phenyl)-5-(4-fluoro-phenyl)-1,5-dihydro-imidazol-2-one and
 (Rac)-4-benzylamino-1-(3-chloro-4-fluoro-phenyl)-5-(4-fluoro-phenyl)-1,5-dihydro-imidazol-2-one.

9. A compound of claim 1, wherein R$^1$ is phenyl substituted by halogen, R$^2$ is phenyl substituted by methoxy and R$^4$ is benzyl.

10. A compound of claim 9, which is
 (Rac)-4-benzylamino-1-(3,4-dichloro-phenyl)-5-(3-methoxy-phenyl) -1,5-dihydro-imidazol-2-one.

11. A compound of claim 1, wherein R$^1$ is phenyl substituted by halogen, R$^2$ is phenyl and R$^4$ is benzyl substituted by halogen.

12. A compound of claim 11, which is
Rac-1-(3,4-dichloro-phenyl)-4-(4-fluorobenzylamino)-5-phenyl-1,5-dihydro-imidazol-2-one.

13. A compound of claim 1, wherein $R^1$ is phenyl substituted by halogen, $R^2$ is phenyl and $R^4$ is lower alkyl.

14. A compound of claim 13, selected from the group consisting of
Rac-1-(3,4-dichloro-phenyl)-4-(3-methyl-butylamino)-5-phenyl-1,5-dihydroimidazol-2-one and
(Rac)-1-(3,4-dichloro-phenyl)-4-hexylamino-5-phenyl-1,5-dihydro-imidazol-2-one.

15. A compound of claim 1, wherein $R^1$ is phenyl substituted by halogen, $R^2$ is phenyl and $R^4$ is —$CH_2$-cycloalkyl.

16. A compound of claim 15, which is
(Rac)-4-(cyclohexylmethyl-amino)-1-(3,4-dichloro-phenyl)-5-phenyl-1,5-dihydro-imidazol-2-one.

17. A pharmaceutical composition comprising a therapeutically effective amount of a compound of formula I

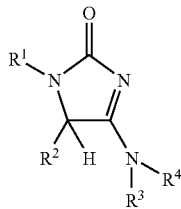

wherein
$R^1$ is —$(CH_2)_n$-aryl or —$(CH_2)_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
$R^2$ is —$(CH_2)_n$-aryl or —$(CH_2)_n$-heteroaryl, wherein such groups are unsubstituted or substituted by one or more substituents selected from the group consisting of lower alkyl, lower alkoxy, halogen and —N(lower alkyl)$_2$;
$R^3$ is hydrogen or lower alkyl;
$R^4$ is —$(CH_2)_n$-aryl or —$(CH_2)_n$-heteroaryl, wherein such groups are unsubstituted or substituted by one or more substituents selected from the group consisting of halogen and lower alkoxy, or is lower alkyl; or
$R^3$ and $R^4$ form together with the N-atom to which they are attached a heterocyclic ring; and
n is 0, 1 or 2;
or a pharmaceutically acceptable acid addition salt thereof and a pharmaceutically acceptable carrier.

18. The composition of claim 17 wherein the compound is a compound of formula IA

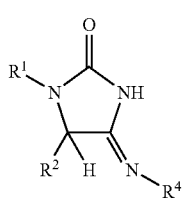

wherein
$R^1$ is —$(CH_2)_n$-aryl or —$(CH_2)_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
$R^2$ is —$(CH_2)_n$-aryl or —$(CH_2)_n$-heteroaryl, wherein such groups are unsubstituted or substituted by one or more substituents selected from the group consisting of lower alkyl, lower alkoxy, halogen and —N(lower alkyl)$_2$;
$R^4$ is —$(CH_2)_n$-aryl or —$(CH_2)_n$-heteroaryl, wherein such groups are unsubstituted or substituted by one or more substituents selected from the group consisting of halogen and lower alkoxy, or is lower alkyl; and
n is 0, 1, or 2;
or a pharmaceutically acceptable acid addition salt thereof and a pharmaceutically acceptable carrier.

19. A process for preparing a compound of formula I

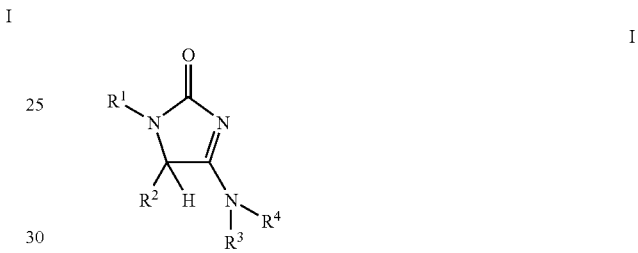

wherein
$R^1$ is —$(CH_2)_n$-aryl or —$(CH_2)_n$-heteroaryl, wherein such groups are unsubstituted or substituted by one or more substituents selected from the group consisting of halogen, lower alkyl substituted by halogen, lower alkoxy, lower alkyl, cyano, nitro, —O-lower alkyl substituted by halogen and morpholinyl;
$R^2$ is —$(CH_2)_n$-aryl or —$(CH_2)_n$-heteroaryl, wherein such groups are unsubstituted or substituted by one or more substituents selected from the group consisting of lower alkyl, lower alkoxy, halogen and —N(lower alkyl)$_2$;
$R^3$ is hydrogen or lower alkyl;
$R^4$ is —$(CH_2)_n$-aryl or —$(CH_2)_n$-heteroaryl, wherein such groups are unsubstituted or substituted by one or more substituents selected from the group consisting of halogen and lower alkoxy, or is lower alkyl, or —$(CH_2)_n$-cycloalkyl; or
$R^3$ and $R^4$ form together with the N-atom to which they are attached a heterocyclic ring; and
n is 0, 1 or 2;
which process is selected from the group consisting of
a) brominating a compound of formula

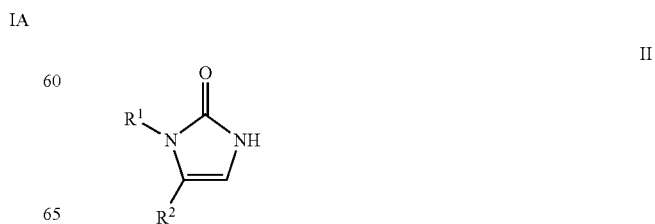

followed by reaction with an amine of formula
NHR³R⁴
to obtain a compound of formula
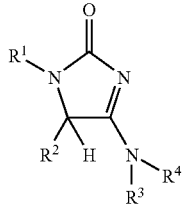
I
and
b) reacting in one step a primary amine of formula $R^2NH_2$ (III), together with potassium cyanate, an isonitrile of formula (V)
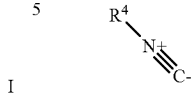
and an aldehyde of formula $R^1C(O)H$ (IV) to obtain a compound of formula I-1
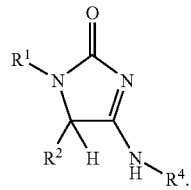
* * * * *